(12) United States Patent
Shen

(10) Patent No.: US 7,956,158 B2
(45) Date of Patent: Jun. 7, 2011

(54) FUSION PROTEINS WITH CLEAVABLE SPACERS AND USES THEREOF

(75) Inventor: Wei-Chiang Shen, San Marino, CA (US)

(73) Assignee: University of Southern California, Los Angeles, CA (US)

( * ) Notice: Subject to any disclaimer, the term of this patent is extended or adjusted under 35 U.S.C. 154(b) by 424 days.

(21) Appl. No.: 12/058,648

(22) Filed: Mar. 28, 2008

(65) Prior Publication Data

US 2008/0299612 A1    Dec. 4, 2008

Related U.S. Application Data

(60) Provisional application No. 60/908,910, filed on Mar. 29, 2007.

(51) Int. Cl.
     *A61K 38/12*     (2006.01)
     *A61K 38/00*     (2006.01)

(52) U.S. Cl. ....................................... 530/317; 530/326

(58) Field of Classification Search ....................... None
See application file for complete search history.

(56) References Cited

FOREIGN PATENT DOCUMENTS

WO      2005034877 A2    4/2005
WO    WO 2005/034877     *    4/2005

OTHER PUBLICATIONS

International Search Report for corresponding PCT application PCT/US08/58789 lists the reference above.

* cited by examiner

*Primary Examiner* — Cecilia Tsang
*Assistant Examiner* — Thomas S Heard
(74) *Attorney, Agent, or Firm* — DLA Piper LLP (US)

(57) ABSTRACT

A polypeptide comprising a first protein domain, a second protein domain, and a dithiocyclopeptide spacer containing at least one protease cleavage site, wherein the dithiocyclopeptide is exogenous relative to the first or second protein domain, and wherein the first and second protein domains are operably linked by the dithiocyclopeptide. Also disclosed are methods of producing the polypeptide and delivering the protein domains into a cell.

19 Claims, 7 Drawing Sheets

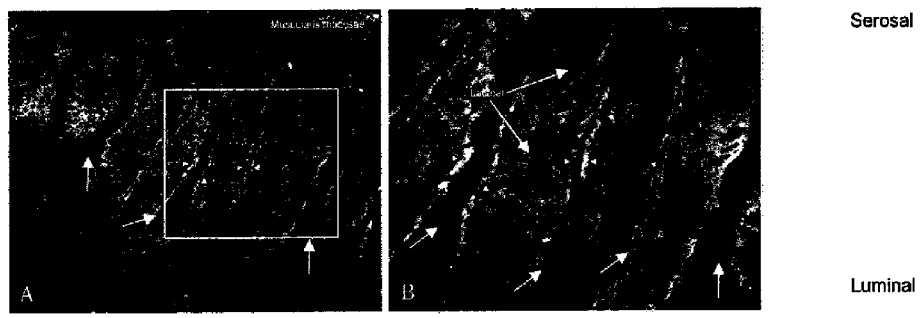
Fig. 1
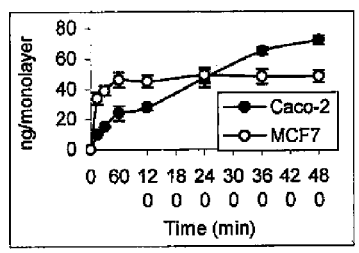
Fig. 2
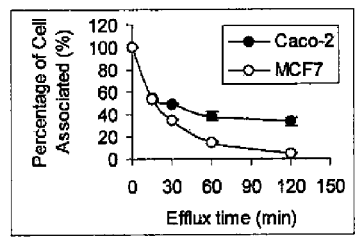
Fig. 3
```
CTC GAG GCT GGT TGT AAA AAT TTT TTC CCT CGT TCT TTT ACT AGT TGT GGT TCT CTC GAG    SEQ ID NO: 5
 L   E   A   G   C   K   N   F   F   P   R   S   F   T   S   C   G   S   L   E    SEQ ID NO: 1
```
Fig. 4

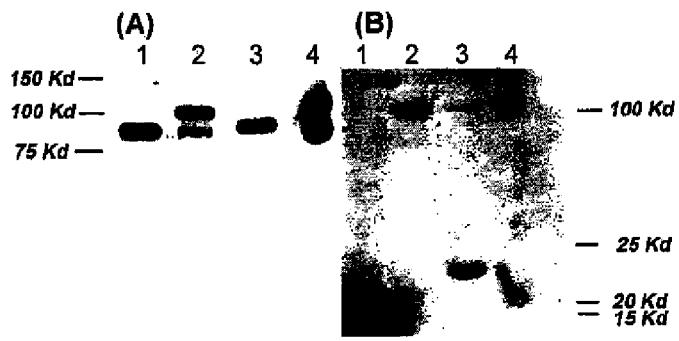
Fig. 5
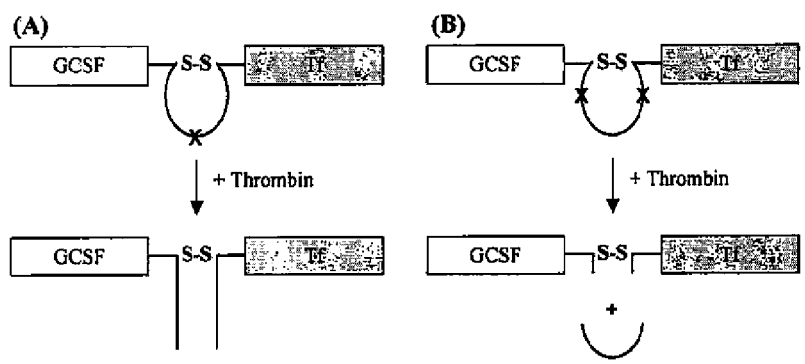
Fig. 6
| (A) | A G C K N F F W K T F T S C | SEQ ID NO: 6 |
| (B) | L E A G C K N F F P R S F T S C G S L E | SEQ ID NO: 1 |
| (C) | L E A G C P R S F W T F P R S C G S L E | SEQ ID NO: 2 |
Fig. 7
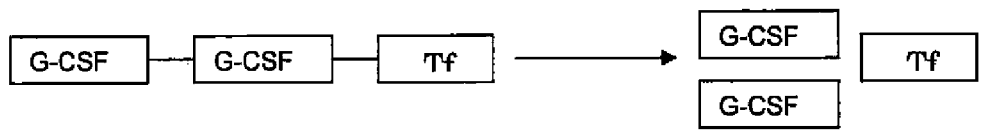
Fig. 8

FUSION PROTEINS WITH CLEAVABLE SPACERS AND USES THEREOF

RELATED APPLICATION

This application claims priority to U.S. Provisional Application Ser. No. 60/908,910, filed on Mar. 29, 2007, the content of which is incorporated herein by reference in its entirety.

FUNDING

This invention was made with support in part by NIH grant R01 GM063647. Therefore, the U.S. government has certain rights.

FIELD OF THE INVENTION

The present invention relates in general to fusion proteins. More specifically, the invention relates to fusion proteins with cleavable spacers and methods of making and using such proteins.

BACKGROUND OF THE INVENTION

The biotech industry has recently made great progress in producing a large number of recombinant human peptides and proteins that possess therapeutic potential. Several of the recombinant proteins such as growth hormones and humanized monoclonal antibodies have already been used clinically to treat human diseases [2]. It is estimated that the protein therapeutic market will grow rapidly at a compound annual growth rate of 10.5%, and will double in market value from 2003 to 2010 [3]. This expansion of protein therapeutics raises many issues in the pharmaceutical industry regarding the formulation and dosage design due to the difference between proteins and small molecular drugs. The most urgent issue to unlock the potential of these new drugs is to develop an oral dosage form for protein drugs, since this route of administration is the most convenient and economical. However, due to the biophysical makeup of protein-based drugs, namely, their large and bulky size, charge and hydrophilicity, and sensitivity to digestive enzymes, achieving oral delivery of these therapeutic agents into the tissues of choice or across epithelial barriers of choice remains difficult [4].

Because most of the protein and peptide drugs today are used for the treatment of chronic diseases, such as insulin for diabetes, frequent injections can cause inconvenience, poor compliance, and adverse side-effects to the patients. Therefore, non-invasive delivery systems for proteins and peptides, especially those utilizing the most convenient oral, route of administration, has long been sought by the pharmaceutical industry.

Despite the great efforts that have been directed towards this area of research, there is no established method for the oral delivery of these drugs. Therefore, there is an urgent need for a novel approach to the design of fusion proteins that can serve as drug delivery systems for delivering pharmaceutically relevant proteins via oral administration.

SUMMARY OF THE INVENTION

The present invention relates to a novel fusion protein that can be used for delivering protein domains into a cell.

In one aspect, the invention features a polypeptide comprising a first protein domain, a second protein domain, and a dithiocyclopeptide spacer containing at least one protease cleavage site. The dithiocyclopeptide is exogenous relative to the first or second protein domain, and the first and second protein domains are operably linked by the dithiocyclopeptide. In some embodiments, the dithiocyclopeptide is cyclized by a disulfide bond. In some embodiments, the dithiocyclopeptide is cleaved by the protease at the protease cleavage site.

A polypeptide of the invention may be a recombinant polypeptide. Accordingly, the invention provides a nucleic acid comprising a DNA sequence encoding a polypeptide of invention and a cell comprising a nucleic acid of the invention.

In another aspect, the invention features a method of producing a polypeptide of the invention. The method comprises cultivating a cell of the invention under conditions that allow expression of the polypeptide. The method may further comprise collecting the polynucleotide or cleaving the polypeptide with the protease.

Also within the invention is a method of delivering protein domains into a cell. The method comprises contacting a cell with a polypeptide of the invention under conditions that allow transport of the polypeptide into the cell. The disulfide bond in the dithiocyclopeptide is reduced during the transport or within the cell, thereby separating the first protein domain from the second protein domain.

In a polypeptide of the invention, the first protein domain may be a granulocyte-colony stimulating factor (G-CSF) domain, the second protein domain may be a transferrin (Tf) domain, and the dithiocyclopeptide may contain a thrombin or trypsin cleavage site, for example, the dithiocyclopeptide may contain LEAGCKNFFPRSFTSCGSLE (SEQ ID NO: 1) or LEAGCPRSFWTFPRSCGSLE (SEQ ID NO: 2). When the second protein domain is a Tf domain, the cell to be contacted with a polypeptide of the invention may be a cell that expresses transferrin receptor (TfR).

Unless otherwise defined, all technical and scientific terms used herein have the same meaning as commonly understood by one of ordinary skill in the art to which this invention pertains. In case of conflict, the present document, including definitions, will control. All publications, patent applications, patents and other references mentioned herein are incorporated by reference in their entirety. The materials, methods, and examples disclosed herein are illustrative only and not intended to be limiting. Other features, objects, and advantages of the invention will be apparent from the description and the accompanying drawings, and from the claims.

BRIEF DESCRIPTION OF THE FIGURES

FIG. 1. Immunofluorescent staining of TfR in a representative frozen section of rat small intestine using anti-rat TfR antibody. The top of the panel is the serosal side and crypt region; the bottom, the luminal side and villi. Arrows indicate the intervillous space and triangles indicate positive TfR staining of enterocytes on the luminal side, predominantly in the lower villous and crypt areas. A) 20×. B) 40× magnification of boxed area in A.

FIG. 2. TfR-mediated cellular uptake of $^{125}$I-Tf. $^{125}$I-Tf was added to Caco-2 or MCF-7 cells in serum-free medium for 15-min incubation at 37° C. Nonspecific uptake was determined in parallel wells containing $^{125}$I-Tf and excess unlabeled Tf. The unbound Tf was removed by three washes of serum-free medium. Cells were then solubilized with 1 N NaOH and assayed for radioactivity. Each data point represents the mean of three measurements with error bars representing standard deviation.

FIG. 3. Pulse-Chase study of Tf in Caco-2 and MCF-7 cells. Post 1 h pre-incubation in serum-free DMEM with 1 mg/ml BSA to remove endogenous Tf, the cells were incubated (pulsed) with $^{125}$I-Tf for at 37° C. for 15 min, rinsed thoroughly, and then incubated with unlabeled Tf at 4° C. for 2 h in serum-free DMEM with 1 mg/ml BSA. Each data point represents the mean of three measurements with error bars representing standard deviation.

FIG. 4. Oligonucleotide insert of the disulfide cyclopeptide linker and its corresponding amino acid sequence. The spontaneous formation of the disulfide bond between Cys-5 and Cys-16 will give a cyclic structure as is observed in somatostatin.

FIG. 5. Western Blots of the fusion protein with a disulfide cyclopeptide linker. (A) anti-Tf; (B) anti-G-CSF. Lane 1: (A) Tf or (B) G-CSF, 2: fusion protein, 3: fusion protein after thrombin digestion and subsequent DTT treatment, and 4: fusion protein after thrombin digestion without DTT treatment.

FIG. 6. The fusion protein with the dithiocyclopeptide spacers. (A) a dithiocyclopeptide spacer with a single thrombin-cutting site, and (B) a dithiocyclopeptide spacer with two thrombin-cutting sites. In both (A) and (B), the reduction of the G-CSF-Tf fusion protein inside the body will separate the G-CSF and Tf domains.

FIG. 7. (A) The structure of somatostatin; (B) The structure of the cyclopeptide spacer. The WKT sequence in somatostatin is replaced by the thrombin-cutting site, PRS. The terminal LE sequence is from the Xho 1 cutting sites in the recombinant plasmid; (C) A hypothetic structure of a somatostatin analog cyclopeptide with two thrombin-cutting sites. The sequence, PRS [45], can be replaced by PRG [34]. The amino acid sequence, FWTF, in (C) will be altered by computer modeling to obtain a stable cyclic structure.

FIG. 8. The multi-GSF fusion protein with in vivo cleavable linkages, such as the disulfide spacer, that can release multiple G-CSF molecules after intestinal absorption. Increased myelopoietic activity can be achieved by this type of fusion protein.

DETAILED DESCRIPTION OF THE INVENTION

Figure 9:
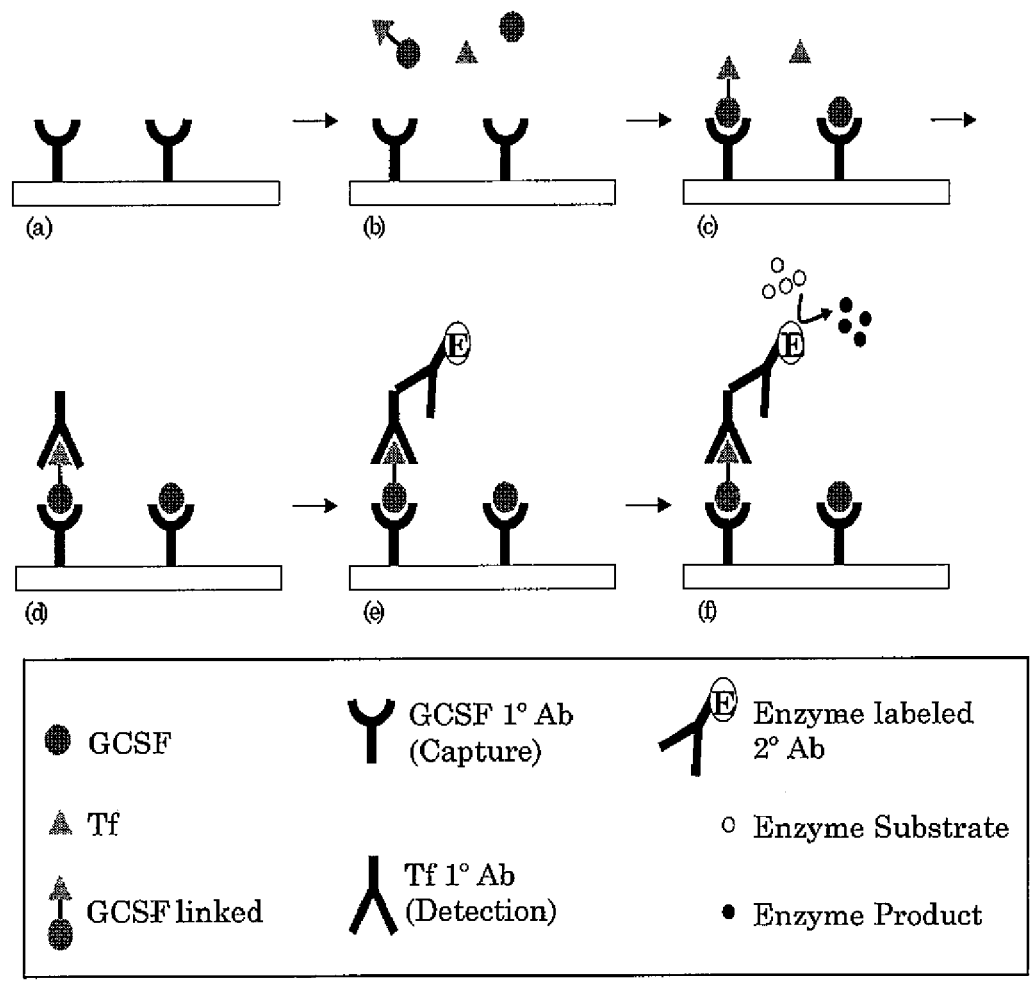
FIG. 9. A rabbit anti-hG-CSF antibody will be immobilized as the first (capturing) antibody, and a goat anti-hTf antibody will be used as the second (detecting) antibody. An enzyme-conjugated third antibody, which will recognize the detecting antibody, will give the signal for the measurement of the concentration of the fusion protein. This assay will allow detecting quantitatively the fusion protein in the presence of a large excess of endogenous Tf and, though less likely, any G-CSF in plasma samples.

This invention is for designing recombinant fusion proteins with two or more domains linked by cleavable spacers that can be separated in vivo in order to achieve the biological activity of each individual component.

Recombinant fusion proteins with protease-cleavable spacers have been used for the in vitro production of recombinant products. For example, the thrombin cutting site has been widely used for linking a recombinant protein with a binding moiety such as glutathione transferase in order to purify the recombinant protein by using affinity chromatography. However, this type of cleavable spacer cannot be used for the design of therapeutic fusion proteins for in vivo separation of the two protein moieties after the administration because (a) it is difficult to achieve a highly specific proteolysis on the spacer peptide only but not on other parts of the fusion protein, and (b) plasma proteases are highly specific, but they are only activated under unique physiological or pathological conditions, such as the presence of plasmin and thrombin in the blood clotting process.

It has been previously demonstrated that the disulfide linkage in protein conjugates was reduced during, but not before, transport across epithelial cell monolayers as well as in the GI epithelium. Therefore, fusion proteins with a disulfide spacer between the two protein moieties will be useful for the separation of the two protein domains inside the body in order to achieve individual biological activity. To this end, an innovative disulfide spacer in the fusion protein has been designed by inserting a disulfide-containing cyclopeptide spacer with a protease-specific cutting site. The fusion protein with the dithiocyclopeptide spacer will then be processed in vitro to convert the spacer into a disulfide-linkage. The general process of this approach is shown as the scheme in FIG. 6, using a recombinant granulocyte colony stimulating factor and transferrin fusion protein, G-CSF-Tf, as an example.

To the inventor's knowledge, there is no recombinant fusion protein with a disulfide or any other cleavable spacers that can separate the domains inside the body.

Even though there is no in vivo cleavable fusion protein available in current biotechnological industry, non-cleavable fusion proteins have been developed for many years. For examples, single chain-Fv proteins (sFv) derived from various antibodies have been used either alone or with other therapeutic proteins as fusion proteins for targeted delivery to antigen-positive cells.

In order to demonstrate the feasibility of producing a reducible disulfide linker between the two domains in a recombinant fusion protein, a plasmid of a fusion protein, G-CSF-Tf, with a disulfide cyclopeptide as the spacer has recently been constructed. The sequence of the disulfide cyclopeptide contains a PRS sequence. The selection of PRS sequence is based on well-studied peptide substrates for thrombin catalysis. The disulfide cyclopeptide linker in the fusion protein is cut by thrombin in vitro to generate a fusion protein with G-CSF and Tf domains linked by a disulfide bond between the two cysteinyl residues in the spacer peptide (FIG. 6). This exposed disulfide bond can be reduced by a reducing agent, dithiothereitol (DTT), and the two domains will be separated only after the reduction.

The method of insertion of the linker peptide between G-CSF and Tf was carried out by standard recombinant procedure. The DNA sequence, as well as its corresponding amino acid sequence, of the cyclopeptide spacer is shown in FIG. 4. The plasmid was transfected in HEK293 cells, and the fusion protein released into the conditioned medium was collected. This fusion protein was subjected to thrombin-treatment and subsequently reduced by DTT.

As shown in FIG. 5, the G-CSF (20 kDa) and Tf (80 kDa) domains in approximately 50% of the fusion protein were still linked together (100 kDa) after thrombin treatment (FIG. 5, Lane 4), indicating a 50% cyclization of the spacer peptide with disulfide bond formation. This assumption was confirmed by the separation of Tf and G-CSF from the thrombin-cut fusion protein after the treatment with DTT (FIG. 5, Lane 3). This result strongly demonstrates that a recombinant fusion protein can be designed with a disulfide linker that will release the active domain, G-CSF, upon reduction.

Accordingly, the invention provides methods for designing recombinant fusion proteins having a cleavable linker that can be cleaved in vivo. The invention also pertains to novel fusion proteins containing cleavable spacers that are capable of being cleaved in vivo.

Polypeptides

A polypeptide of the invention (i.e., a G-CSF-dithiocyclopeptide-Tf fusion protein) comprises a first protein domain (e.g., a G-CSF domain), a second protein domain (e.g., a Tf domain), and a dithiocyclopeptide spacer containing at least one protease cleavage site. The dithiocyclopeptide is exogenous relative to the first or second protein domain, and the first and second protein domains are operably linked by the dithiocyclopeptide.

As used herein, a "protein domain" refers to a wild-type protein of interest, or a variant of the protein that retains a biological function of the wild-type protein. The size of a protein domain of the invention may be 10-100, 20-90, 30-80, 40-70, or 50-60 kDa. Variants of a protein of interest may be constructed by, for example, substituting or deleting residues not needed for a biological function of the protein or by inserting residues that will not affect a biological function of the protein. Generally, substitutions should be made conservatively, i.e., the most preferred substitute amino acids are those having physiochemical characteristics resembling those of the residues to be replaced. Examples of conservative substitutions include substitution of one aliphatic residue for another, such as Ile, Val, Leu, or Ala for one another, or substitution of one polar residue for another, such as between Lys and Arg, Glu and Asp, or Gln and Asn. Other such conservative substitutions, for example, substitution of an entire region with another having similar hydrophobicity characteristics, are well known in the art. Moreover, particular amino acid differences between proteins of different species (e.g., human, murine and other mammals) are suggestive of additional conservative substitutions that may be made without altering the essential biological characteristics of the protein. The activity of a protein domain may be determined using any of the methods known in the art for that protein.

For example, a "G-CSF domain" is a protein domain that retains the biological functions of G-CSF, i.e., promoting the proliferation, survival, maturation and functional activation of cells from the neutrophilic granulocyte lineage. In some embodiments, a G-CSF domain may have the wild-type amino acid sequence of a G-CSF protein (e.g., a human G-CSF protein). In other embodiments, a G-CSF domain may be a variant of the wild-type G-CSF. G-CSF variants may be constructed using the methods described above. The activity of a G-CSF domain may be determined using any of the methods known in the art. For example, a NFS-60 MTT proliferation assay may be employed as described in the examples below.

A "Tf domain" is a protein domain that retains the biological functions of Tf, i.e., binding and transporting iron. In some embodiments, the Tf domain may have the wild-type amino acid sequence of a Tf protein (e.g., a human Tf protein). In other embodiments, the Tf domain may be a variant of the wild-type Tf. Tf variants may be constructed using methods described above. The activity of a Tf domain may be determined using any of the methods known in the art. For example, the activity of a Tf domain may be determined by measuring its ability to bind a TfR.

A "dithiocyclopeptide" is a peptide containing two thiol groups that can be oxidized to form an intramolecular disulfide bond and a ring-like structure. The disulfide bond may be reduced, e.g., either in vivo or in vitro. A dithiocyclopeptide may have 5-50, 10-40, or 20-30 amino acids. A dithiocyclopeptide of the invention contains at least one protease cleavage site. Proteases and their cleavage sites are commonly known in the art. For example, PRS may be used as a cleavage site for thrombin. The first and second protein domains are operably linked by the dithiocyclopeptide. By "operably" is meant that the loop of the dithiocyclopeptide, when inserted between the first and second protein domains, should be exposed and accessible for protease digestion, intramolecular disulfide bond formation, and reduction of the disulfide bond. A polypeptide of the invention may contain multiple copies of the protein domains operably linked by dithiocyclopeptide spacers. The design of a polypeptide of the invention is described in detail below in the examples.

A polypeptide of the invention may be chemically synthesized or produced as a recombinant protein. For production of a recombinant protein, a DNA encoding the polypeptide is constructed and transcribed into an mRNA. The mRNA is then translated into the recombinant protein. To facilitate production of the recombinant protein, a secretion signal may be added at the N-terminus of the protein. The recombinant protein will then be secreted from a cell into the culture medium and can be collected accordingly. The order of the G-CSF domain and the Tf domain in a polypeptide of the invention may vary. In some embodiments, the G-CSF domain may be located to the N-terminus of the Tf domain. In other embodiments, the G-CSF domain may be located to the C-terminus of the Tf domain.

When linked to a Tf domain, the G-CSF domain is transported into and across a cell through the TfR pathway. It is more efficient than transport of a G-CSF protein by itself. Transcytosis is the uptake of material at one face of a cell by endocytosis, its transfer across a cell in vesicles, and its discharge from another face by exocytosis (Alberts et. al. (2002) Molecular Biology of the Cell, $4^{th}$ edition, Garland Science, p. G-35). Transport and transcytosis of a polypeptide of the invention and the G-CSF domain may be measured and compared using any of the methods known in the art.

Nucleic Acids

The invention also provides a nucleic acid containing a DNA sequence encoding a polypeptide of the invention. Such a nucleic acid may be constructed using recombinant DNA technology well known in the art.

For example, a nucleic acid of the invention may be a vector containing a DNA sequence encoding a polypeptide of the invention. The vector can be used for production of the polypeptide. As used herein, the term "vector" refers to a nucleic acid capable of transporting another nucleic acid to which it has been linked. Various types of vectors are well known in the art. See, e.g., U.S. Pat. Nos. 6,756,196 and 6,787,345. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain expression vectors are capable of directing the expression of genes to which they are operatively linked.

The recombinant expression vectors are suitable for expression of a polypeptide of the invention in a host cell. These vectors include one or more regulatory sequences, selected on the basis of the host cells, operatively linked to a nucleic acid sequence encoding a polypeptide of the invention. Within a recombinant expression vector, "operatively linked" means that the nucleic acid sequence of interest is linked to the regulatory sequences in a manner which allows for expression of the nucleic acid sequence (e.g., in an in vitro transcription/translation system or in a host cell when the vector is introduced into the host cell). "Regulatory sequences" refers to promoters, enhancers and other expression control elements (e.g., polyadenylation signals). Such regulatory sequences are described, for example, in Goeddel, supra. Regulatory sequences include those which direct constitutive expression of a nucleic acid sequence in many types of host cell and those which direct expression of a nucleic acid sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors can be introduced into host cells to thereby produce a polypeptide of the invention. They can be designed for expression of the polypeptide in prokaryotic or eukaryotic cells, e.g., bacterial cells such as E. coli, insect cells (using baculovirus expression vectors), yeast cells, or mammalian cells. Suitable host cells are discussed further in Goeddel, Gene Expression Technology Methods in Enzymology 185, Academic Press, San Diego, Calif. (1990). Alternatively, the recombinant expression vector can be transcribed and translated in vitro, for example, using T7 promoter regulatory sequences and T7 polymerase.

In some embodiments, a polypeptide of the invention may be expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187-195). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells, see Chapters 16 and 17 of Sambrook et al. eds., Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the polypeptide preferentially in a particular cell type (e.g., tissue-specific regulatory elements are used to express the polypeptide). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740 and Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the alpha-fetoprotein promoter (Campes and Tilghman (1989) Genes Dev. 3:537-546).

Cells

Another aspect of the invention pertains to host cells into which a nucleic acid of the invention has been introduced. The terms "host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the invention can be expressed in bacterial cells such as E. coli, insect cells, yeast or mammalian cells (such as Chinese hamster ovary cells (CHO) or COS cells). Other suitable host cells are known to those skilled in the art.

A nucleic acid can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the DNA encoding a polypeptide of the invention. Preferred selectable markers include those which confer resistance to drugs, such as G418, hygromycin and methotrexate. A nucleci acid encoding a selectable marker can be introduced into a host cell on the same vector as that encoding a polypeptide of the invention or can be introduced on a separate vector. Stably transfected cells can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the invention. Accordingly, the invention provides a method for producing a polypeptide of the invention using the host cells of the invention. In one embodiment, the method comprises culturing the host cell of the invention in a suitable medium such that the polypeptide is produced. In another embodiment, the method further comprises isolating the polypeptide from the medium or the host cell. Methods for cell culture and protein expression and purification can be found, e.g., in Sambrook et al. (supra) and other laboratory manuals.

Compositions

A polypeptide of the invention can be incorporated into pharmaceutical compositions suitable for administration. Such compositions typically comprise the polypeptide and a pharmaceutically acceptable carrier. As used herein, the language "pharmaceutically acceptable carriers" include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. In addition, the composition may include stabilizing agents such as sodium bicarbonate, BSA, and casein.

A pharmaceutical composition of the invention may be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the polypeptide in the required amount in an appropriate solvent with one or a combination of ingredients enumerated above, as required, followed by filtered sterilization. Generally, dispersions are prepared by incorporating the polypeptide into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the polypeptide can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compositions can also be prepared in the form of suppositories (e.g., with conventional suppository bases such as cocoa butter and other glycerides) or retention enemas for rectal delivery.

In some embodiments, a polypeptide of the invention is prepared with carriers that will protect the polypeptide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the polypeptide and the particular therapeutic effect to be achieved, and the limitations inherent in the art of compounding such a polypeptide for the treatment of individuals.

A pharmaceutical composition of the invention can be included in a container, pack, or dispenser together with instructions for administration.

Uses

A polypeptide of the invention with a disulfide spacer between the two protein domains is useful for the separation of the two domains inside a cell or body in order to achieve individual biological activity. To this end, an innovative disulfide spacer in the polypeptide is designed by inserting a disulfide-containing cyclopeptide spacer with a protease-specific cutting site. The polypeptide with the dithiocyclopeptide spacer is processed in vitro to convert the spacer into a disulfide-linkage. When a cell or body is contacted with the processed polypeptide, the disulfide bond in the dithiocyclopeptide spacer is reduced during the transport of the polypeptide into the cell or when the polypeptide is inside the cell. The two protein domains are separated and function individually.

A polypeptide of the invention may be used according to the functions of the protein domains to be delivered into a cell. For example, G-CSF has been found to be useful in the treatment of conditions where an increase in neutrophils will provide benefits. See, e.g., U.S. Pat. No. 6,790,628. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture (for example, for bone marrow transplants or ex vivo expansion). G-CSF has been administered to transplant patients as an adjunct to treatment of infection or for treatment of neutropenia (Diflo et al. (1992) Hepatology 16:PA278, Wright et al. (1991) Hepatology 14:PA48, Lachaux et al. (1993) J. Ped. 123:1005-1008, and Colquehoun et al. (1993) Transplantation 56:755-7580).

For protein domains that have pharmaceutical functions, the invention provides a treatment method involving administering to a subject in need thereof an effective amount of a composition of the invention. A subject to be treated may be identified in the judgment of a subject or a health care professional, and can be subjective (e.g., opinion) or objective (e.g., measurable by a test or diagnostic method). The term "treating" is defined as administration of a substance to a subject with the purpose to cure, alleviate, relieve, remedy, prevent, or ameliorate a disorder, symptoms of the disorder, a disease state secondary to the disorder, or predisposition toward the disorder. An "effective amount" is an amount of the substance that is capable of producing a medically desirable result as delineated herein in a treated subject. The medically desirable result may be objective (i.e., measurable by some test or marker) or subjective (i.e., subject gives an indication of or feels an effect).

The effective amount of a composition of the invention is between 0.001 and 300 mg/kg body weight, 1-4 times every two weeks. The effective amount can be any specific amount within the aforementioned range, wherein the lower boundary is any number of mg/kg body weight between 0.001 and 299, inclusive, and the upper boundary is any number of mg/kg body weight between 0.002 and 300, inclusive. The effective amount is useful in a monotherapy or in combination therapy for the treatment of relevant disorders. In particular, a dose of 5 µg/kg body weight may be used for human injection and a dose of 50 µg/kg of body weight may be used for oral administration in human. As the skilled artisan will appreciate, lower or higher doses than those recited above may be required. Effective amounts and treatment regimens for any particular subject (e.g., a mammal such as human) will depend upon a variety of factors, including the age, body weight, general health status, sex, diet, time of administration, rate of excretion, drug combination, the severity and course of the disease, condition or symptoms, the subject's disposition to the disease, condition or symptoms, and the judgment of the treating physician or veterinarian.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

Example I

Using receptors as targets and receptor-binding ligands as vectors for transcellular transport is a promising way of achieving selective delivery of peptide and protein drugs across the intestinal epithelium [7]. This process, termed receptor-mediated transcytosis, is highly specific because it enhances only the transport of molecules that are conjugated to receptor-binding ligands [8]. Receptor-mediated transcytosis is an inherent cellular process in epithelial and endothelial cells [9]. Unlike most current approaches, which use penetration enhancers such as bile salts and lipids to increase epithelial insulin absorption [10], a receptor-mediated transcytotic process does not change the structure of the plasma membranes or the intercellular junctions, and conceivably has fewer unwanted side-effects and safety concerns.

TfR has been utilized for the development of orally administered, receptor-mediated delivery systems for peptide and protein drugs for the following reasons: a) TfR density has been found to be very high in human [1,1] and rat GI epithelium [12]. Utilization of even a fraction of this receptor pool can potentially result in significant delivery of Tf-conjugated peptides across the GI mucosal barrier. The high density of TfR in intestinal epithelial cells makes TfR a better vehicle than other receptors with low density, such as cobalamin-intrinsic factor receptors [13], for the GI absorption of a therapeutically effective dose of peptide drugs. b) Tf is a natural carrier protein for iron [14]. Hence, unlike the binding of hormones or growth factors to their receptors, the binding of Tf to TfR will not alter any major metabolic or physiologic functions within the cell. c) Diferric Tf has been found to be a relatively stable glycoprotein in the GI tract. Enzymes such as chymotrypsin, which are responsible for the degradation of a majority of the proteins and peptides in the GI tract, have a low degradative action on the Tf molecule [15]. d) The mechanism in which Tf deposits iron in the cells has been well characterized [16]. There are many studies published on immunohistochemical detection for tissue distribution of TfR, both TfR and TfR2, each indicating the presence of the receptors in the small intestine. Generally, TfR staining is strongest in the crypt region and decreases moving along the entire villous axis [17]. However, perhaps due to differences in tissue isolation and fixation methods, localization differs slightly [16]. Due to the area of localization in intestinal epithelial cells, it is generally believed that TfR is not directly involved in the major iron absorption from the diet [18]. However, recent findings indicate that TfR can serve as a regulator of iron absorption in GI epithelia via the TfR-mediated endocytosis/transcytosis pathway, although the exact molecular mechanisms have not been established [19]. Furthermore, the possibility of a transient appearance of TfR on the luminal side as a result of membrane mis-sorting due to the recycling protein transport pathway in intestinal epithelial cells [20] can also induce an apical-to-basolateral TfR-mediated transcytosis for the GI absorption of protein drugs. Therefore, a further understanding of the intracellular processing and regulation of TfR at the target sites, such as the intestinal epithelium for oral absorption, that govern the destiny of internalized Tf will result in ever increasing applications of TfR as a pharmaceutically relevant marker for drug delivery.

During recent years, TfR has been developed as a potential ligand to enable drug targeting and delivery of therapeutic agents that would normally suffer from poor pharmacokinetic characteristics [21]. TfR-directed targeting has enabled the efficient delivery of therapeutic agents to sites of interest, including the central nervous system [22] and malignant tissues [23, 24]. In addition, by utilizing knowledge of the intracellular sorting and recycling pathways of TfR, including Rab and PI(3)K mediated processes [25, 26], one can maximize the transepithelial delivery of peptide-based therapeutics. Depending upon the desired result, apparently paradoxical effects can be achieved. For example, TfR-based strategies can selectively achieve either an accumulation of the carried drug within targeted tissues, or the delivery of the therapeutic entity across tissues of interest [27]. Previous studies unequivocally demonstrated that Tf-based chemical conjugation could be applied for non-invasive delivery of therapeutic proteins across the absorptive barriers, such as the small intestinal [28] and alveolar epithelial [29] cells, which express TfR on the surface. More importantly, a hypoglycemic effect was observed from using orally administered insulin-Tf conjugate in streptozotocin-induced diabetic rats [5, 30]. Similarly, an increase of neutrophil number was observed when a Tf conjugate of G-CSF was administered orally to BDF1 mice [6, 29]. However, the major obstacle with the chemical conjugation methodology is that the chemically cross-linked products are mostly heterogeneous mixtures of various size and composition [29] and, conceivably, are not suitable as therapeutic drugs. In addition, the high cost of preparing Tf chemical conjugates with a reasonable purity also prohibits developing them into marketable drugs. To overcome these obstacles, the possibility of using recombinant DNA technology to prepare fusion proteins that consist of both Tf and therapeutic protein moieties for transport and biological activity was explored.

Fusion proteins consisting of anti-TfR antibody and protein drugs have been developed for TfR-mediated transcytosis across blood-brain barrier endothelial cells [22, 31]. Anti-TfR antibody, rather than Tf, was chosen as the carrier for this blood to central nervous system transport model due to the high level of endogenous Tf in the blood. It was reasoned that for oral administration, since there is very little endogenous Tf in the gastrointestinal (GI) tract, the construction of fusion proteins with a Tf, rather than anti-TfR, moiety should be suitable for the development of protein drugs in oral delivery. To demonstrate the feasibility of using a Tf-fusion protein for oral drug delivery, a recombinant plasmid consisting of cDNA from both human Tf and human G-CSF was recently prepared [1]. After transfecting this plasmid into HER 293 cells in culture, a protein from the conditioned medium with a molecular weight of approximately 100 kD, which was positive in Western blotting assay for both Tf (MW: 80 kD) and G-CSF (MW: 19 kD), was isolated. More importantly, this fusion protein showed a marked effect on the increase of absolute neutrophil count (ANC) when orally administered to BDF1 mice [1]. The findings on the oral bioavailability of recombinant Tf-G-CSF fusion protein have given rise to great expectations by others for the future development of protein drugs [32].

Even though the feasibility of using Tf-fusion proteins as oral drugs has been demonstrated, there are several issues that must be addressed before Tf-fusion proteins can be applied toward future clinical utilization. First, it was found that the in vitro biological activities of both Tf and G-CSF moieties were less than 10% of each of the original proteins [1]. Although this in vitro activity was significantly higher than that of the intact chemical conjugate as previously reported [6], it indicates that the oral efficacy of the Tf-fusion protein delivery system would be even higher if a G-CSF-Tf fusion protein with improved in vitro activity could be obtain. Furthermore, many protein drugs may not be pharmacologically active if they are covalently linked to Tf. These limitations can be solved by inserting a linker peptide, either cleavable or non-cleavable in vivo, between the Tf and the therapeutic protein moieties. Linker peptides have been widely used to reduce the interaction between two moieties in a fusion protein [33]. In addition, linker peptides with a specific thrombin-cutting site can also be designed to separate the two domains in the fusion protein by thrombin treatment [34]. Recently published results on the insertion of helical peptide spacers in G-CSF-Tf clearly demonstrate that a significant improvement of both in vitro and in vivo biological activity of a recombinant fusion protein can be achieved by increasing the distance between the two functional domains [35]. Furthermore, the success in the preparation of disulfide-linked fusion proteins from previous studies provides the opportunity to achieve an in vivo separation of the active domain, G-CSF, from the carrier domain, Tf. Previous studies in chemically conjugated Tf either with insulin or as the aggregated Tf by the disulfide linkage demonstrated that free protein drugs were released by the disulfide-reduction reaction during or after the transport across intestinal epithelial cells [30, 41]. Therefore, it is very likely that a fully activated G-CSF can be released from the fusion protein into the blood circulation. To the inventor's knowledge, this is the first example of a fusion protein that has been designed to release the functional domain in vivo via disulfide reduction, even though the disulfide bond is one of the most commonly used linkages in preparing chemical conjugates in drug delivery [36]. A fusion protein with such an in vivo cleavable spacer between the two domains can have many other applications. One application is to prepare fusion proteins with multiple functional domains, such as a multi-G-CSF-Tf fusion protein which will release many active G-CSF molecules from a single Tf-fusion protein. Conceivably, a multiple functional domain fusion protein will greatly reduce the dosage and improve the therapeutic efficacy in oral delivery.

Besides the in vitro and in vivo activity, other chemical, biochemical, and pharmacikinetic properties are also important for determining the bioavailability and therapeutic properties of the fusion protein in oral absorption. One of the major concerns is the stability of the fusion protein against proteolysis in the GI tract [37]. As reported by others, Tf is resistant to trypsin and chymotrypsin degradation [15]. Most recent results on insulin-Tf conjugates indicated that Tf can also protect insulin from chymotrypsin digestion [41]. Therefore, it is very likely that the stability of the G-CSF domain in the fusion protein is also better than that of free G-CSF in the GI tract. Another concern may be the toxicity of the fusion protein either locally or systemically. The toxicity of Tf has not been considered because the amount of Tf in human body is very high, i.e., approximately 240 mg/kg with half of it in the blood [42]. Therefore, it is unlikely that the amount of Tf absorbed as part of the fusion protein, possibly at the ng/ml levels, would cause any adverse effect. Similarly, G-CSF is a natural hematopoietic growth factor that has been used clinically for many years [43]. The more serious side effects of G-CSF, such as splenomegaly and osteoporosis, occur only in chronic administration [43]. There is no reason to believe that these side effects will be enhanced by oral administration of the fusion protein because none of them is associated with the GI tract [43].

Finally, like other protein drugs, the immunogenicity of the fusion protein should be addressed. Since the fusion protein G-CSF-Tf consists of human Tf and human G-CSF, the immunogenicity in humans is difficult to be evaluated in the mouse BDF1 model. It is generally believed that the immune system responds to dietary proteins by inducing oral tolerance which will lead to non-responsiveness to the antigens [38]. Therefore, it is unlikely that a fusion protein of human G-CSF and Tf will become a strong oral immunogen either in animal models or in humans.

In summary, based on previous findings on the oral delivery of insulin-Tf in diabetic rats and G-CSF-Tf in BDF1 mice, it is believed that Tf could be used as a delivery vehicle to improve the GI absorption of other peptide and protein drugs. Recent findings on the recombinant G-CSF-Tf fusion protein, with either cleavable or non-cleavable peptide spacers, further demonstrate that it is feasible to design a recombinant protein with both oral absorption and therapeutic effectiveness. In this current application, one object is to investigate the optimization of the pharmacological activity, as well as the mechanism of transport, of the Tf-fusion protein in order to fully explore the potential for the application in oral therapeutics. This innovative transport process of Tf-fusion proteins will provide a unique opportunity to develop a new generation of protein drugs that can be administered via the oral route for treating human diseases. The impact of such a drug delivery system on cost-effectiveness and patient compliance in long-term pharmaceutical care, to say the least, would be enormous.

Detection of TfR in Rat Intestines

Frozen sections of rat small intestine were prepared and fixed in 3.7% formaldehyde for 15 min at RT, rinsed with PBS and then quenched with 50 mM NH$_4$Cl. Following blocking with 10% FBS, tissue samples were incubated with monoclonal anti-TfR antibody (50 µg/mL OX26 in 1.5% FBS in PBS) for 1 h at RT, washed with PBS and then incubated for 1.5 h at RT with a FITC-conjugated goat anti-mouse secondary antibody (1:100). The slides were washed in PBS and mounted with prolong antifade for fluorescence microscopy. FIG. 1 shows the intact villi with positive TfR staining of enterocytes on the luminal side, predominantly in the lower villous and crypt areas. This also demonstrates that some TfR may be transiently present on the luminal surface. In addition to this result, there are many studies published of immunohistochemical detection for intestinal tissue distribution of TfR, both TfR, and TfR2, each indicating TfR staining is strongest in the crypt region and decreases moving along the entire villous axis [17, 44].

Evidence of Tf-Accumulation in Caco-2 Cells

Results from recent studies of the in vivo pharmacological effect of Tf conjugates or fusion proteins indicate that there is a sustained release of the protein drugs into the blood stream after oral absorption via TfR-mediated transcytosis [1]. To identify the intestinal epithelial cells as the potential depot for the Tf-conjugates, enterocyte-like Caco-2 cells were used as a model to investigate the intracellular processing of internalized Tf. The cellular uptake of Tf was compared in Caco-2 cells and, as a control, MCF-7 mammary carcinoma cells. A linear increase in cellular uptake of $^{125}$I-Tf was observed in Caco-2 cells, but not in MCF-7 cells, which reached a plateau within one hour as is expected when a rapid recycling of TfR occurs (FIG. 2). In addition, the pulse-chase study also indicated that there was an accumulation of Tf in Caco-2 cells but not in MCF-7 cells (FIG. 3). These findings suggest that apically-internalized Tf is retained longer in an intracellular compartment in Caco-2 cells, and this retention is not detected in MCF-7 cells. Since the intracellular retention of Tf has not been reported in other cell culture studies, and has only been mentioned recently as a regulatory mechanism for the intestinal absorption of iron [18], it demonstrates that the sustained release of orally absorbed Tf is due to the storage of Tf in the intestinal epithelial cells.

Recombinant G-CSF-Tf Fusion Protein with the Insertion of Disulfide Cyclopeptide Sequences In order to demonstrate the feasibility of producing a reducible linker between the two domains in a recombinant fusion protein, a plasmid of G-CSF-Tf with a disulfide cyclopeptide as the spacer has recently been constructed. The sequence of the disulfide cyclopeptide was based on that of somatostatin (FIG. 7), with the replacement of the sequence of amino acid 8-10, WKT, by a thrombin-specific sequence, PRS. The selection of PRS sequence was based on well-studied peptide substrates for thrombin catalysis [45]. It is believed that the replacement of Lys(8)-Thr(9) in somatostatin by Arg-Ser would have a minimal effect on the peptide conformation because both the positive charge and the hydroxyl group are preserved. Therefore, the only significant change in the sequence was the replacement of Trp(7) in somatostatin by proline to concur with the specificity of thrombin [34, 45]. It was believed that this somatostatin-like peptide sequence between G-CSF and Tf should cyclize spontaneously. The disulfide cyclopeptide linker in the fusion protein could be cut by thrombin in vitro to generate a fusion protein with G-CSF and Tf domains linked by a disulfide bond between the two cysteinyl residues in the spacer peptide (FIG. 6). This exposed disulfide bond could be reduced during or after the GI absorption and, therefore, the two domains would be separated in the blood circulation.

The method of insertion of the linker peptide between G-CSF and Tf is described below. The DNA sequence, as well as its corresponding amino acid sequence, of the cyclopeptide spacer is shown in FIG. 4. The plasmid was transfected in HEK293 cells, and the fusion protein released into the conditioned medium was collected as described below. This fusion protein was subjected to thrombin-treatment and subsequently reduced by DTT.

As shown in FIG. 5, the G-CSF and Tf domains in approximately 50% of the fusion protein were still linked together (100 kDa) after thrombin treatment (FIG. 5, Lane 4), indicating a 50% cyclization of the spacer peptide with disulfide bond formation. This assumption was confirmed by the separation of Tf and G-CSF from the thrombin-cut fusion protein after the treatment with DTT (FIG. 5, Lane 3). This result strongly demonstrates that a recombinant fusion protein can be designed with a disulfide linker that will release in vivo the active domain, G-CSF, upon reduction.

The application of biotechnological products as therapeutic drugs for the treatment of human diseases is limited by the poor absorption of proteins and peptides across mucosal barriers, most noticeably the intestinal epithelial cells. Thus, protein and peptide drugs are almost exclusively administered through injection. Since most of these drugs are used for the treatment of chronic diseases, such as insulin for diabetes, frequent injections can cause inconvenience, poor compliance, and adverse side-effects to the patients. Therefore, to develop non-invasive delivery systems for proteins and peptides, especially the most convenient oral route of administration, has long been sought by the pharmaceutical industry. Despite the great efforts that have been directed towards this area of research, there is no established method for the oral delivery of these drugs.

As a continuous effort to investigate transferrin receptor (TfR)-mediated transcytosis in the gastrointestinal (GI) tract, a transferrin (Tf) and granulocyte colony-stimulating factor (G-CSF) fusion protein (G-CSF-Tf) has been recently prepared by using recombinant technology [1]. This fusion protein not only possesses both TfR-binding and cell proliferative activity in vitro, but also oral myelopoietic activity in vivo. These findings offer a new approach in the development of recombinant therapeutic proteins with oral bioavailability. However, the fusion protein maintained only a small fraction of the in vitro biological activity of either G-CSF or Tf. Therefore, one object is to investigate the spacers between G-CSF and Tf moieties in the fusion protein to optimize biological activities. The spacers especially with the cleavable linkage are important for extending the findings to other therapeutic proteins which may not be active in the Tf-fusion protein form. Furthermore, another object is to investigate the pharmacokinetics and biodistribution of orally administered G-CSF-Tf for improving therapeutic efficacy. An additional object is to elucidate the mechanism and to exploit the application of the sustained myelopoietic effect of orally absorbed G-CSF-Tf.

In order to achieve these goals, the following will be carried out:

1. Preparing G-CSF-Tf constructs with different spacers to improve in vitro biological activities.
   a. To design and produce fusion proteins with reducible disulfide spacers, including fusion protein with multiple G-CSF domains;
   b. To test the in vitro bioactivity of the fusion proteins from (a):
      i. TfR-binding assay in Caco-2 cells;
      ii. Cell proliferative assay in NFS-60 cells.
2. Comparing in vivo myelopoietic activity—subcutaneous versus oral routes:
   a. To investigate selected fusion proteins for their myelopoietic effects with subcutaneous and oral administration in BDF1 mice;
   b. To investigate the effect of dietary iron on the accumulation and transport of the fusion protein in the GI epithelium.
3. Measuring pharmacokinetics (PK) and biodistribution of the fusion protein:
   a. To detect the plasma concentration of selected fusion proteins after oral administration;
   b. To detect the tissue distribution of orally administered fusion protein;
   c. To elucidate the transport mechanism, deposition, and bioavailability of selected fusion proteins.

The pharmacokinetics and oral bioavailability of G-CSF-Tf, as well as the technology for controlled release of G-CSF from the fusion protein, will be established in BDF1 mice. The long term goal is to develop transferrin-fusion proteins into a new class of protein drugs that can be administered orally by patients. Results from this invention will also provide important information for the design of therapeutic recombinant proteins with other routes of administration for the treatment of various human diseases.

Preparation G-CSF-Tf Constructs with Different Spacers to Improve In Vitro Biological Activities The fusion protein, G-CSF-Tf, exhibited less than 10% of the in vitro TfR binding and cell proliferation activity as compared to G-CSF and Tf individually. Since this fusion protein included a very short spacer, i.e., Leu-Glu, which is not cleavable, it is likely that the in vitro activity is an indication of the in vivo myelopoietic effect, which can be improved upon. Therefore, Tf-binding and NFS-60 cell proliferation assays can be performed for the selection of active fusion proteins.

One approach for improving the biological activity is to insert a spacer, which will separate the Tf and G-CSF domains in the fusion protein and, consequently, decrease interference of the binding to each respective receptor. On the other hand, it is also possible to insert a spacer that can be cleaved in the body so that an unmodified protein drug can be released, where subsequently a complete recovery of the biological activity can be achieved. A cleavable spacer could be important for delivery of protein drugs that require transport from the blood to the specific tissue for the pharmacological action. Both approaches will be utilized to improve the effect of the G-CSF-fusion protein. Previous results obtained from the fusion protein spacers will be used as a guideline for the design of optimal spacers for fusion proteins. Additionally, the use of computer modeling techniques to aid in the design and evaluation of various linkers will allow quick and cost efficient selection for in vitro testing. Constructs with predicted active protein structures will be selected and transfected in HEK293 cells for the production of the fusion proteins. The products will then be subjected to both TfR-binding and NFS-60 cell proliferation assays to verify biological activity. Only those fusion proteins with high biological activity will be further tested for in vivo myelopoietic activity in mice.

Design and production of G-CSF-Tf with cleavable spacers. Fusion proteins with protease-cleavable spacers are generally designed for the in vitro production of recombinant products. For example, the thrombin cutting site has been widely used for linking a recombinant protein with a binding moiety such as glutathione transferase in order to purify the recombinant protein by using affinity chromatography [49]. However, this type of cleavable spacer is not very practical for in vivo separation of the two protein moieties after oral administration for two reasons: (a) it is difficult to achieve a highly specific proteolysis of the spacer only after the GI absorption of the fusion protein, and (b) plasma proteases are highly specific, but they are mostly activated under unique physiological or pathological conditions, such as the presence of plasmin and thrombin in the blood clotting process.

It has been previously demonstrated that the disulfide linkage in protein conjugates was reduced during, but not before, transport across epithelial cell monolayers as well as in the GI epithelium [29, 41]. Therefore, fusion proteins will be designed with a disulfide spacer between the two protein moieties that will be accessible for reduction as observed in the chemical disulfide conjugates (FIG. 6). An innovative disulfide spacer in the fusion protein will be designed by inserting a disulfide-containing cyclopeptide spacer with a thrombin-specific cutting site. The fusion protein with the dithiocyclopeptide spacer will then be processed in vitro to convert the spacer into a disulfide-linkage.

The choice of the cyclopeptide spacer should fufill three criteria. First, the peptide sequence should spontaneously form a cyclic conformation. Second, the peptide sequence should contain a thrombin-specific cutting site with a high efficiency. Third, the loop of the cyclopeptide spacer, when inserted between G-CSF and Tf, should be exposed and accessible for thrombin digestion and disulfide reduction. Therefore, the peptide will be designed based on the sequence of natural occurring cyclopeptides. For example, salmon calcitonin contains a cycloheptapeptide and somatostatin contains a cyclododecapeptide, both rings being formed by a disulfide linkage. The 14-amino acid cyclopeptide, somatostatin, is particularly interesting because it contains two lysyl residues in a 12-amino acid ring and would be easy to introduce a highly selective cutting site for thrombin (FIG. 7(A)). The cyclopeptide spacer was based on the structure of somatostatin (FIG. 7(B)), and has demonstrated (a) the spontaneously cyclization of the spacer in the fusion protein, and (b) the accessibility to thrombin-cutting and disulfide reduction to separate Tf and G-CSF.

There are several potential concerns in the design of the disulfide spacer. First, even though highly reactive thrombin-cutting site can be screened from the amino acid sequence, there are many lysyl and arginyl residues in proteins that may possess a low activity toward thrombin cutting. Therefore, the fusion protein after thrombin cleavage will be analyzed by SDS-PAGE to verity that the two protein moieties are intact. If thrombin can digest the protein at sites other than the cyclopeptide spacer, other specific proteases, such as factor Xa [34] will be considered for the in vitro processing. Furthermore, it has been reported that recombinant proteases can possess very high restriction on an amino acid sequence [50]. If a different protease will be used to process the fusion protein, the sequence of the cyclopeptide will be altered to present a new specific cutting site. However, results from the study of the cyclopeptide-spaced fusion protein indicated that both Tf and G-CSF are not sensitive to thrombin digestion. Therefore, the non-specific digestion by thrombin is not an issue for the current study.

The results showed that approximately 50% of the fusion protein remained as the intact 100 kDa protein after thrombin treatment. This result strongly supports the feasibility of the design of the cleavable spacer with disulfide linkage generated by thrombin-cutting of the cyclic peptide for the in vivo release of free G-CSF upon reduction of the disulfide spacer. However, this result also shows that the other 50% of the fusion protein has been converted to free Tf and G-CSF upon thrombin digestion, indicating an incomplete disulfide cyclization in the product. There are two possibilities for the incomplete formation of the disulfide bond between the two cysteinyl residues in the spacer peptide. First, the HEK295 cells were grown in protein-free medium for the production of the fusion protein. It is highly possible that some types of reducing agents have been included in the medium to maintain the viability of the cells (the manufacturer was unwilling to disclose the contents in the protein-free medium). In this case, the product should be reoxidized under mild conditions after being harvested from the medium. The re-oxidation of denatured proteins to form the disulfide bonds has been well studied [51], and the procedures to examine the cyclization of the spacer peptide in the fusion protein will be followed. The other possibility is that the replacement of WKT by PRS sequence may alter the somatostatin conformation and increase the energy of the disulfide formation. In this case, the conformation of the cyclic peptide spacer in FIG. 7(B) will be subjected to further structure modeling as described below. Attempts will be made to replace one or two amino acids to minimize the energy for the cyclic conformation while preserve the thrombin specificity.

Computer modeling will be performed for initial examination of potential cleavable spacers, including peptides in FIG. 7. Multiple conformations of the spacers will be constructed. For natural cyclic peptides, these will include the experimentally observed conformers). Conformers will be generated without an S—S bridge, since the purpose of the procedure is to examine the conformational flexibility of the linearized peptide. A similar procedure will be used to vary the spacer conformation, and the criteria for selection of potential spacer sequences will be as follows: 1) the proximity of the cysteine side chains; 2) the accessibility of the thrombin cutting site, and 3) the relative energy of the fusion protein in conformations that meet criteria 1 and 2, compared to other folds that do not meet these criteria. Following initial selection of potential spacers, molecular dynamics simulations will be performed to examine the behavior of the fusion protein in a solvated environment.

The other concern regarding the disulfide spacer is the generation of new antigenic epitopes. For example, the cyclopeptide spacer as shown in FIG. 7(B) will generate two peptides after thrombin digestion, with the sequences of LEAGCKNFFPR (SEQ. ID NO: 3) and SFTSCGSLE (SEQ ID NO: 4) each attached to a domain of the fusion protein. These two peptides may induce the formation of highly specific anti-hapten antibodies. This problem would be an issue if the drug were to be used chronically, even though the chance of developing hypersensitivity toward ingested proteins is very low. One way to avoid this potential problem is the introduction of two thrombin cutting sites in each cyclopeptide spacer. As shown in FIG. 6(B), it is possible that a disulfide cyclopeptide can be designed so that very short peptide chains will remain at the spacer. Shorter peptides should decrease the chance of eliciting immune response. FIG. 7(C) shows a hypothetical peptide derived from somatostatin structure that possesses two thrombin-cutting sites. Extensive computer modeling of the conformation by altering the FWTF sequence will be performed in order to yield the most stable cyclic conformation that can promote the disulfide bond formation in the spacer peptide.

Production of Recombinant Fusion Proteins.

(i) The insertion of a Linker Sequence into the G-CSF-Tf Plasmid

Annealed synthetic phosphorylated oligonucleotides will be used to create the linker consisting of double strand DNA between G-CSF and Tf. The linkers will be designed with sticky ends that are complimentary with the xho1 cutting site. The oligonucleotides will be dissolved in TE buffer to a final concentration of 20 pmol/μl. 1 μl of each oligonucleotide solution (both forward and reverse sequences) will be mixed with 2 μl (10×) annealing buffer (100 mM Tris HCl, pH7.5, 1 M NaCl, 10 mM EDTA) and ddH$_2$O will be added to make a final volume of 20 µl. The mixture will be heated to 95° C. for 10 min, and allowed to cool down gradually to room temperature to form the double-stranded DNA with 5'-overhangs that are complimentary to the xho 1 cutting site. The double-stranded DNA linkers will be ligated to the xho 1-cutted G-CSF-Tf plasmid that has been treated with phosphatase (CIP). The linker-vector ratio and the ligation temperature will be adjusted to control the copies of linker inserted. 5 µl ligation mixture will be used to transform JM109 competent cells. The transformed clones will be selected on ampicillin-agar plates. The plasmids will be isolated and tested by restriction endonuclease digestion followed by PCR amplification. Several plasmids will be constructed and the sequences of the constructs will be verified by DNA sequencing.

(ii) Expression of Fusion Proteins with Different Linkers

Monolayer grown HEK293 cells will be transfected with different plasmids by using Lipofectamine-2000 (Invitrogen). After 5 h incubation, the protein free medium CD293 will be replaced. The conditioned medium will be collected after a 5-day culture. The conditioned medium will be collected and subjected to the analysis of 10% SDS/PAGE. The proteins will be transferred to cellulose nitrate membrane. Goat anti-human serum Tf antibody and anti-human G-CSF antibody will be used as primary antibodies. Horseradish peroxidase-conjugated anti-goat IgG antibody will be used as the secondary antibody, and peroxidase activity will be detected by the enhanced chemiluminescence (ECL) method.

(iii) Expression of Tf-Fusion Proteins with Dissociable Multi-G-CSF Domains

One of the limitations of using Tf-fusion protein for oral delivery of protein drug is that each fusion protein molecule contains one of each of Tf and drug domain. Since the molecular weight of Tf (80 kDa) is relatively larger than most drug proteins (~20 kDa), the dosage size for the fusion proteins will be several folds higher than that of the free drug protein. For example, 5-fold higher dosage size has been used for G-CSF-Tf than G-CSF itself because the molecular weights for these two proteins are 100 and 20 kD, respectively. Therefore, if a multiple-domain G-CSF fusion protein could be prepared (e.g., 2 G-CSF to one Tf as shown in FIG. 8), the dosage size of the protein drug would be decreased significantly.

To prepare a multiple G-CSF fusion protein, it is essential that the G-CSF domains in the fusion protein can be separated from each other in order to individually exert their therapeutic action. This requirement is now achievable with the most recently developed disulfide cyclopeptide linkers. A fusion protein that consists of 2 G-CSF domains per each Tf domain all tandem linked by disulfide cyclopeptide spacer will be prepared. After in vitro processing by thrombin-cutting, the fusion protein will release 2 G-CSF molecules after intestinal absorption (FIG. 8). A 2-fold increase of the in vivo myelopoietic efficacy should be observed in the G-CSF fusion protein with two G-CSF domains.

Testing of Fusion Proteins in NFS-60 Cell Proliferation Assays and TfR-Binding.

(i) G-CSF-Dependent NFS-60 Cell Proliferation

The G-CSF activity of the fusion protein will be measured by NFS-60 cell proliferation assay [1, 6, 35]. Fusion proteins with the dithiocyclopeptide spacers will be processed by thrombin treatment before testing their biological activity. NFS-60 cells will be washed three times with RPMI-1640/10% FBS and aliquoted into 96-well microtiter plates at a density of $1 \times 10^5$ cells/ml. Subsequently 10 µl of 10-fold serial dilutions of the G-CSF and fusion protein will be added. The plates will be incubated at 37° C. in a 5% $CO_2$ incubator for 48 h. A MTT (3-(4,5-dimethylthiazol-2-yl)-2,5-diphenyl tetrazolium bromide) assay will be performed essentially as described [52]. Briefly, the cells will be treated with 1 mg/ml MTT in serum-free and phenol red-free RPMI 1640 media for 4 h. The formazan crystals that form will be dissolved in isopropanol and absorbance will be measured at 570 nm on a TECAN GENios Plus microplate reader. Fusion proteins with a disulfide spacer, including those with multi-G-CSF domains, will be reduced by DTT before the addition to the culture medium of NFS-60 cells for the assessment of the in vitro effect in cell proliferation. An extensive dilution of the DTT-treated fusion protein is required to avoid the effect of high DTT concentration on the cell-proliferation assay.

(ii) TfR Binding Activity

Human Tf will be radiolabeled with $^{125}$I (ICN, Irvine, Calif.) using chloramine-T catalyzed iodination, followed by purification using Sephadex G-50 column chromatography, and subsequently dialyzed in phosphate buffered saline (PBS, pH 7.8). Caco-2 cells will be seeded in 12-well cluster plates until fully differentiated. Caco-2 monolayers will be washed with cold PBS three times, and then incubated in serum-free D-MEM supplemented with 0.1% BSA at 37° C. for 30 min to remove the endogenous Tf. A mixture of 3 µg/ml $^{125}$I-Tf with 3-, 10- or 30-fold of unlabeled fusion protein or Tf in D-MEM with 1 mg/ml BSA will be added to different wells. Similar to section (i), fusion proteins with disulfide cyclopeptide spacers will be processed by thrombin-treatment before testing the TfR-binding activity. After 30 min of incubation at 4° C., the medium will be removed, and the cell monolayers will be washed three times with cold PBS. The cells will then be dissolved in 1 M NaOH, and the lysates will be counted in a gamma counter. Unlike the cell proliferation assay described in (i), intact disulfide-spaced fusion proteins without DTT reduction should be used for TfR binding assay.

Comparison of In Vivo Myelopoietic Activity—Subcutaneous (Sc) Versus Oral (po) Routes Investigation of selected fusion proteins for their myelopoietic effects with sc and po administration in BDF1 mice. It is believed that the in vivo myelopoietic activity of most fusion proteins of G-CSF and Tf should correlate with the in vitro biological activity. This assumption will be verified by selecting different fusion proteins for oral administration in mice. As suggested in a recent publication [35], a good correlation between the in vitro biological activity and the in vivo myelopoietic activity in fusion proteins with non-cleavable spacers is expected. However, in the case of fusion proteins with cleavable spacers, even after the thrombin-treatment, the in vivo myelopoietic activity may not always correlate to the in vitro biological activity, unless the thrombin-processed fusion protein will be further reduced into two separate domains before the in vitro assays. When injected subcutaneously, both cleavable and non-cleavable fusion proteins will be transported into the blood vessel, and a similar myelopoietic activity may be exhibited because the plasma half-life of the protein-protein disulfide bond is about 7-8 h [53]. On the other hand, when administered orally, fusion proteins with a disulfide-spacer may be reduced in either the intestines or the liver to release the free G-CSF into the blood circulation. In this case, the rate of free G-CSF releasing may be faster than the transport process of the intact fusion protein from intestines to the blood. Since the plasma half-life of G-CSF is considerably shorter than that of Tf, the released G-CSF will have a shorter plasma half-life than that of the intact fusion protein. Therefore, a higher potency but a shorter duration of the myelopoietic activity in orally administered disulfide-spaced fusion protein is expected.

The in vivo myelopoietic activity of the disulfide-spaced fusion protein will be compared with that of the chemically linked disulfide conjugate which will be prepared as previously described [6]. Since there are many potential side-reactions that may occur to the protein structure during the chemical modification with cross-linking reagents, a higher in vivo efficacy from the fusion proteins than the chemically linked conjugates is expected. This assumption is based on the previous observation that the fusion protein [1] was more effective than the chemically linked disulfide conjugate [6] for the increase of ANC in BDF-1 mice. However, different linkages between G-CSF and Tf were used in those studies, i.e., non-cleavable and cleavable linkage for the fusion protein [1] and the chemical conjugate [6], respectively. Therefore, the comparison between a disulfide-spaced fusion protein and a disulfide-linked conjugate should give a more accurate assessment of efficacy for in vivo myelopoietic activity.

Male BDF1 mice (Charles River Laboratories, Wilmington, Mass.), 6-8 weeks of age, will be used in all animal experiments described in this report. The BDF1 mouse model will be used for the studies because of previous experience with this model for assessing human G-CSF responses [1, 6, 35]. In addition, unlike other commercially available chemotherapy- or radiation-induced neutropenia mouse models (e.g., Perry Scientific, Inc., San Diego, Calif.), BDF1 mice are normal animals and will be a good model to study the physiological GI absorption without the interference of the complications associated with drug or radiation treatment. The current application focuses on the optimization and the mechanism of the GI absorption of Tf-fusion proteins. However, neutropenia mouse models will be considered in the future when the therapeutic efficacy of G-CSF fusion proteins will be evaluated for further development.

BDF1 mice will be allowed to acclimate for 5 days. Animal experiments will be compliant with the 'Principles of Laboratory Animal Care' (NIH Publication #85-23) and has been approved by the Institutional Animal Care and Utilization Committee at the University of Southern California. Prior to dosing, the mice will be fasted for 12 h. The treatment groups will receive a single dose on day 0. Due to the difference in molecular weight, i.e., 20 kD for G-CSF and 100 kD for the fusion protein, animals will receive the dose based on equivalent μmoles. For subcutaneous administration, 5 mg/kg (0.05 μmol/kg) of the fusion protein or 1 mg/kg (0.05 μmol/kg) of G-CSF was injected. For oral administration, 50 mg/kg (0.5 μmol/kg) fusion protein or 10 mg/kg (0.5 μmol/kg) G-CSF will be given via a gavage needle. All mice will be fed 4 h after the treatment.

Blood samples will be collected daily from the tail vein, diluted 20-fold and lysed in an acidic crystal-violet solution (0.1% crystal violet, 1% acetic acid, in water). Since the size of each blood sample will be less than 20 uL and the time between each collection will be 24 h, the same mice will be used for the entire experiment without any problem. From the diluted blood samples, the total white blood cell (WBC) count will be determined manually with a hemacytometer. The percentage of polymorphonuclear neutrophils (PMN) among the leukocytes will be determined manually by using Wright-stained blood smear glass slides that will be examined under an Olympus BH-2 microscope. The absolute neutrophil count (ANC) will be determined by multiplying the total WBC count by the PMN percentage [1, 6].

Investigation of the effect of dietary iron on the accumulation and transport of the fusion protein in the GI epithelium. A sustained myelopoietic effect of the orally administered G-CSF-Tf fusion protein in BDF1 mice has been observed [1]. This observation suggests that there is likely a depot site in the GI for the fusion protein. Previous results also indicate the accumulation of Tf in cultured Caco-2 cells, which is contradictory to the rapid recycle pathways of TfR in other cell lines. These findings, together with recent reports by others on the role of apo-Tf in GI absorption of dietary iron [19], suggest that there may be a depot compartment for apo-Tf in intestinal epithelial cells which can be regulated by the uptake of iron from the mucosal membrane via the divalent metal transportor 1 (DMT1). Such a regulatory mechanism will provide a method of controlled release of Tf-fusion protein from GI epithelia to the blood circulation which conceivably would be an important factor for the future development of oral protein drugs. A sustained release may be advantageous for some protein drugs such as growth hormones, while rapid delivery to the blood circulation may be required for others such as insulin.

To validate the belief, G-CSF-Tf will be orally administered to BDF1 mice together with a subtoxic dose of iron at 1 g/kg. The major concern of oral feeding of iron to mice is the toxicity. However, carbonyl iron is very safe when administered orally to animals. It has been reported in that a single dose of 2 g of carbonyl iron per rat (approximately 10 to 20 g/kg) demonstrated no ill effect [55]. In addition, bioavailability of carbonyl iron is greater than 50% in relative to ferrous sulfate [55]. Therefore, it is estimated that an oral dose of carbonyl iron at 1 g/kg should produce a high intestinal absorption of iron with low toxicity in mice. Alternatively, if carbonyl iron exhibits any solubility problem, other highly soluble ferrous compounds such as ferrous gluconate ($LD_{50}$: 3.7 g/kg orally in mice, the Merck Index) can be used. The myelopoietic effect of the orally administered G-CSF-Tf, either with or without iron supplement, will be examined. The number of days post administration that will produce the highest ANC, as well as the value of ANC, will be compared between these two groups. It is expected to see a shortened effective time for the myelopoietic effect with possibly a higher ANC in mice that receive the iron-supplemented dose. If this result can be confirmed, a similar study will be repeated by giving the iron supplement at different days after the oral administration of G-CSF-Tf. It is expected to observe a boost in the myelopoietic effect of G-CSF-Tf for the time points when iron-supplement is given, e.g., first and second days. Such a booster effect should alter the pharmacodynamic properties and the bioavailability of G-CSF-Tf and this information will be used to elucidate the transport, deposition, and bioavailability of G-CSF-Tf.

Measurement of Pharmacokinetics (PK) and Biodistribution of the Fusion Protein

It was demonstrated in a recent report that oral administration of G-CSF-Tf maintained an increased ANC in mice for 4 to 5 days, while only 1 day for G-CSF [1]. Since the life span for neutrophils is only about 12 h, the finding implies that either the plasma half-life of G-CSF-Tf is significantly longer than that of G-CSF, or there is a sustained release mechanism of G-CSF-Tf transport from the intestine to the blood stream. The fact that subcutaneously injected G-CSF and G-CSF-Tf have a similar effect on neutrophil counts may suggest that the prolonged effect of orally administered G-CSF-Tf is most likely due to a sustained release rather than the plasma half-life [1]. It is believed that orally administered G-CSF-Tf is transported across the GI epithelium and, subsequently, to the liver via the portal vein. G-CSF-Tf will accumulate either in the intestinal epithelium or in the liver, possibly as an apo-Tf form, followed by a slow release into blood circulation as the diferric form [1]. At the present time, it is believed that intestinal epithelium, rather than the liver, is more likely the retention site for the sustained release of orally absorbed G-CSF-Tf. The reason is that, once delivered into the portal vein, the fusion protein will be mixed with a high concentration of endogenous Tf in the blood before reaching the liver. Such a dilution effect will unlikely make G-CSF-Tf selectively retained in the liver. If this is true, the release of intestinal epithelial cell-associated G-CSF-Tf should be able to be manipulated by varying the amount of dietary iron given to the experimental mice.

To verify the belief, the pharmacokinetics and the biodistribution of orally administered fusion proteins will be investigated. In order to simplify the interpretation of the results, the non-cleavable fusion protein, G-CSF-Tf, will be used as the model drug because it should remain intact in the body. An initial accumulation of G-CSF-Tf in the intestine after oral administration, with a subsequent release to the blood circulation over approximately 3 days, is anticipated. Since the possibility that the liver may also play a role in the sustained release of G-CSF-Tf cannot be completely ruled out, both intestinal and liver retention will be investigated in the initial study.

Detection of blood concentration of orally administered fusion protein in mice. There are commercial RIA and ELISA kits available for both G-CSF and Tf that are highly specific for human G-CSF or human Tf. Therefore, the plasma level of G-CSF-Tf after oral administration in mice should be able to be directly detected. However, since the concentration of the fusion protein in the plasma will be very low, the cross-reactivity between human protein and mouse protein is a serious concern. Therefore, commercial immunoassay kits will be screened to make sure that the detection of human G-CSF and Tf can be carried out in the presence of mouse serum. On the other hand, the fusion protein is a unique molecule which consists of both the G-CSF and Tf structure, and it has been demonstrated that each moiety in the fusion protein can be recognized by its corresponding antibody in Western blot [1]. Therefore, a simple ELISA method that will be highly sensitive and specific only to the fusion protein, but not G-CSF or Tf should be able to be developed.

To develop a G-CSF-Tf-specific ELISA, a rabbit anti-human G-CSF antibody will be selected to be immobilized as the first (capturing) antibody, and a goat anti-hTf antibody as the second (detecting) antibody. Mouse antibody for the first 2 antibodies will be avoided because mouse serum will be used as samples for analysis. A horseradish peroxidase-conjugated sheep anti-goat immunoglobulin antibody will be used as the signal antibody. The procedure for the assay method (FIG. 9), which is similar to that in ELISA assay, is well-established [56, 57] and several immunoassays have been previously developed. Since a combination of anti-G-CSF and anti-Tf antibodies will be used, a highly sensitive and specific ELISA can be developed for measuring the concentration of the intact fusion protein, regardless of the spacers, in mouse plasma without the interference from endogenous G-CSF or Tf. For the measurement of free G-CSF that is released from the cleavable fusion proteins, a commercial ELISA kit for human G-CSF will be used, which, in principle, should also detect the fusion protein. However, the level of free G-CSF can be estimated by subtracting the concentration of G-CSF-Tf (using anti-fusion protein assay) from that of total G-CSF (anti-G-CSF assay).

(i) Pharmacokinetics of Orally Administered G-CSF-Tf.

Male BDF-1 mice, 6-8 weeks of age, 5 mice per group, weighing 22-25 g, will be administered orally with the fusion proteins at a dose of 50 mg/kg (10 mg/kg of G-CSF equivalent). This dose will be used first in the pharmacokinetic studies to ensure that a significant and reliable measurement will be obtained. Five mice from each treatment group will be sacrificed at 4 h, 8 h, 12 h, 24 h and 48 h post-administration. Any time point shorter than 4 h or longer than 48 h may not be necessary due to the previous observation of the slow intestinal absorption of proteins and the decrease of myelopoietic effect after 48 h. However, shorter or longer time points will be included for future studies if the results from the initial studies warrant the addition of more time points.

The blood samples, as well as the liver and intestines of each mouse, will be collected. The liver and intestinal samples will be saved for the further study of tissue localization. Plasma will be isolated from each blood sample and subjected to ELISA analysis of either the intact fusion protein or free G-CSF as described above. Since the myelopoiesis of G-CSF has been shown to have a ceiling effect [58], the dose should be within the linear response range. The simple, non-cleavable fusion protein, G-CSF-Tf, will be used first. Depending on the initial results, the dose of the protein and the time points can be adjusted if necessary. Controls will be done in mice that are injected intravenously with G-CSF-Tf at $\frac{1}{10}$ of the oral dose and blood will be collected according to a similar sampling schedule. The plasma half-life of G-CSF-Tf from po and iv treatment will be compared, and a prolonged plasma half-life for the po administration will indicate that a sustained release occurs with the oral absorption route of the fusion protein.

To further investigate whether repeated oral administration will change the GI absorption of G-CSF-Tf, an experiment to measure the plasma levels of G-CSF-Tf as described above is planed, except that there will be 10 mice per group. The number of blood samples may be reduced to only 2 to 3 time points, depending on the results that will be obtained in the PK studies. At each time point after oral administration of the fusion protein, 5 mice from each group will be sacrificed to collect blood for G-CSF-Tf measurement. The other 5 mice in each group will be dosed orally with G-CSF-Tf once every week for a total of 4 weeks. The multiple-dosed mice will be sacrificed after the fourth week administration at the same time points. The plasma levels of G-CSF-Tf will be measured and will be compared with that of the mice from the first week. Since it is known that TfR is not subjected to either up- or down-regulation by Tf-binding, it is not expected to find any difference in G-SCF-Tf plasma levels between the single and the multiple dosed groups. However, if difference is found, the possibility of mucosal immunological or toxicological response to the orally administered G-CSF-Tf will be considered.

To assess the toxicity of orally administered G-CSF-Tf, the intestine of each mouse in the control and multiple-dosed group will be fixed and the microscopic examination will be performed. Since it is not known what symptoms are associated with the toxicity of either Tf G-CSF, or the fusion protein, general morphological changes that may indicate GI toxicity will be looked for [59, 60, 61]. Initially, the decrease of the length of the villi, as well as the number of mitotic cells in the cryptic region, can be used as an indication of the toxicity. Furthermore, an increase of myeloperoxidase activity and/or the intraepithelial lymphocytes will suggest a mucosal immune response. However, any observation of mucosal immune response should be interpreted carefully, because a fusion protein of human Tf and G-CSF will be used in a mouse model.

One of the pitfalls for this study is that it is difficult to maintain G-CSF-Tf in the diferric form, especially under the acidic environment in the stomach. Tf and apo-Tf may be processed differently in the body and may show difference in absorption. There is ample evidence indicating that apo-Tf is accumulated inside intestinal epithelial cells much longer than diferric Tf as a mechanism of iron absorption [62]. Such a selective retention may also occur in hepatocytes where apo-Tf is converted to Tf and recycled back to the blood [63]. Therefore, the iron-binding status may affect the release and, consequently, the efficacy of the orally administered fusion protein. To avoid the variation, all fusion proteins will be kept in the apo-Tf form by pre-incubation with a potent iron chelator, desferroxamine [64], followed by dialysis. Apo-G-CSF-Tf will also be the control for iv injection.

(ii) Pharmacokinetics of Orally Administered G-CSF-SS-Tf.

Similar studies will be carried out with mice orally administered with the disulfide-spaced fusion protein, G-CSF-SS-Tf. The oral and intravenous doses will be the same as those of G-CSF-Tf. Fusion proteins with a disulfide spacer may release G-CSF either during the transepithelial transport or in the liver and may have different pharmacokinetic properties from that of non-cleavable G-CSF-Tf. It is possible that the plasma level of G-CSF is dependent upon the reduction of the disulfide spacer rather than the release of the intact fusion protein during the transport process. Therefore, it is expected to find a higher efficacy of G-CSF-SS-Tf than G-CSF-Tf when orally administered to BDF1 mice, assuming the efficiencies of receptor-mediated transport of these two fusion proteins are similar. To verify this belief the plasma level of both free and fusion protein-associated G-CSF will be measured by using the two types of ELISA. The results will provide guidelines on the dose and time points for the study. There are three possible outcomes from this study: only G-CSF is detectable, only G-CSF-SS-Tf is detectable, and both G-CSF-SS-Tf and G-CSF are detectable. In the case that only G-CSF is detectable, it is important to estimate its plasma half-life. Because it is known that the plasma half-life of G-CSF in mice is about 2.5 h [65], a prolonged plasma half-life of G-CSF in G-CSF-SS-Tf treated mice will suggest a sustained release mechanism in the oral absorption pathway. On the other hand, if only G-CSF-SS-Tf is detectable, it will suggest that the disulfide spacer in the fusion protein is not accessible for reduction during transport, and the plasma levels of G-CSF-TF and G-CSF-SS-Tf following their respective oral administration should be similar. In this case, if there is a difference between the efficacy of G-CSF-Tf and G-CSF-SS-Tf, it is most likely due to subsequent reduction of the disulfide spacer in the target tissues. However, if both G-CSF and G-CSF-SS-Tf are detectable, the ratio of concentrations of these two forms of G-CSF at various time points and their respective half-life will be determined. It is expect to see the plasma half-lives of the fusion protein and the regenerated G-CSF are significantly longer than that of G-CSF when administered directly to mice (2.5 hr). Based on the plasma pharmacokinetic profiles of G-CSF, G-CSF-SS-Tf and G-CSF-Tf, a mechanism of transport and release of fusion proteins will be able to be postulated.

(iii) Analysis of Pharmacokinetic Measurements

Various data sets will be fitted using a computer program (e.g., WinNonlin) to obtain relevant pharmacokinetic parameters such as the area under the curve (AUC), apparent plasma half-life ($t_{1/2}$), mean residence time (MRT), maximum plasma concentration ($C_{max}$) and time to reach maximum plasma concentration ($t_{max}$). The absolute bioavailability will be calculated by dividing the AUC value of the plasma fusion protein from oral administration by that from intravenous injection, and normalized by the doses in the two different routes of delivery. The difference in $t_{max}$ will provide evidence for the sustained release mechanism. The difference in plasma concentration of the two fusion proteins in treated and control mice, by either oral or intravenous administration, will be evaluated either by independent t-test or analysis of variance (ANOVA). This comparison will be performed for each time point. The statistic significance at the later time points is important to indicate the difference in sustained release rates. If the null hypothesis was rejected in ANOVA, Tukey's test will be used for multiple comparisons. Values will be considered statistically significant if $p<0.05$.

Detection of the tissue distribution of orally administered fusion protein. The prolonged myelopoietic effect of orally administered G-CSF-Tf [1], which was also observed in previous studies with the oral administration of Tf-conjugates of insulin [5] and G-CSF [6], suggests that there is a sustained release mechanism involved in the transport process. A high retention of Tf in cultured Caco-2 cells, a cell line that is generally considered as a model of enterocytes has been detected. Therefore, it is possible that the site of depot for orally administered G-CSF-Tf is in the intestinal epithelial cells. Previous study also confirmed the retention of orally administered Tf-aggregate in intestines [41]. However, since the retention of Tf in the liver has also been reported [63] and confirmed in previous studies [41], the possibility that the liver may also play a role in the controlled release of G-CSF-Tf cannot be ruled out. It is believed that Tf-based fusion proteins will be retained first in the intestinal epithelial cells, and subsequently, in the liver. However, it is not clear whether the retention in intestinal epithelium or in the liver is the rate-limiting step for the release of G-CSF-Tf into the bloodstream. The controlled release mechanism will be verified by using both radioiodine-labeled Tf and the specific ELISA that will be developed for detection of G-CSF-Tf fusion protein.

(i) Kinetics of Localization of Orally Administered $^{125}$I-Tf in the Intestine and the Liver Previous results showed a high localization of $^{125}$I-Tf-aggregates in both the intestine and liver when orally administered in mice [41]. However, in order to evaluate the significance of these localization results, the experiment will be repeated by using $^{125}$I-Tf in both apo- and diferric forms, and the kinetics of the distribution in long-term time points such as 2, 3 and 4 days post-administration will be investigated. The entire intestine or liver, as well as an aliquot of blood sample, will be counted in a gamma counter. The radioactivity will be plotted versus the time for all three compartments and a preliminary kinetics of the distribution will be determined. An important control for this study is the distribution of iv injected $^{125}$I-Tf in the intestine and liver. This control will provide a background measurement of radioactivity as well as for the retention. From this experiment, it will be found out whether or not orally administered apo-Tf and diferric-Tf are different in intestine- and liver-localization. Furthermore, it will be found out whether the intestine or the liver is the major location for the retention of the orally administered Tf. If a higher localization is observed in the intestine than in the liver for the long-term time points, it will suggest that retention in the intestine is possibly the rate-limiting step for the sustained release of the fusion protein into the circulation. On the other hand, if there is more radioactivity in the liver, then the retention in the liver is likely the depot of the orally administered fusion protein.

There are several pitfalls in this study. First, it is recognized that the measurement of radioactivity may be misleading due to the degradation products from $^{125}$I-Tf. In addition, there may be dehalogenation reactions that occur in the intestine and/or the liver, which may remove $^{125}$I from Tf Finally, free $^{125}$I or the degradation products may incorporate into tissue components and give a false positive result for this study. Therefore, even though using $^{125}$I-Tf as a tracer is simple and sensitive, the data obtained from this study will be considered only as preliminary results. However, this study will provide guidelines for the design of further studies as described in the next two sections.

(ii) Detection of the Localization of Orally Administered Biotin-Tf in the Intestine and Liver To further verify that the tissue localization of radioactivity is indeed the intact Tf, studies will be carried out by using a biotinylated Tf, biotin-Tf, which will be prepared by using the commercially available EZ-Link™ Sulfo-NHS-LC-Biotin conjugation kit from Pierce.

Biotin-Tf will be administered orally to mice. Mice orally administered with biotinylated serum albumin (Biotin-SA) will be used as controls. At various time points, mice will be sacrificed, and the intestine and liver will be collected. Both intestine and liver will be sliced in a cryogenic microtone and subjected to examination under a fluorescent microscope by using FITC-avidin. Biotin-SA-fed mice will be used as the background measurement. In addition, biotin-Tf can be detected quantitatively by using the biotin-avidin-based enzyme immunoassay. This assay has been previously used to measure the amount of biotin-Tf in the plasma of mice orally administered with biotin-Tf [41]. For the detection of biotin-Tf in intestines and livers, extracts from tissue homogenates will be subjected to the biotin-avidin immunoassay.

It is reasonable to believe that biotin-Tf should be processed identically as G-CSF-Tf in the GI tract. Therefore, that the fusion protein is indeed retained in the intestine or the liver will be able to be verified. However, biotin-Tf can only provide a qualitative determination of the location of orally administered Tf. It cannot be used for either the quantitative measurement of tissue localization or the kinetic study of the transport of the fusion protein in the GI tract. For a more complete study of the localization and the quantity of G-CSF-Tf in the intestine or liver, the ELISA method that will be developed will need to be used.

(iii) Quantitative Measurement of the Accumulation of Orally Administered G-CSF-Tf in the Intestine and Liver In this experiment, mice will be administered orally with G-CSF-Tf. At various time points, the mice will be sacrificed, and the intestine and liver, as well as the blood, will be collected. Intestines and livers will be weighed and subsequently homogenized in PBS, and the tissue extracts will be collected as the supernatant fraction after centrifugation. ELISA procedure will be performed based on the estimated concentration of $^{125}$I-Tf. The amount of G-CSF-Tf will be presented as ng/g wet tissue. Results from this study will be used to compare with those from the study described above, and both the quantity and the kinetics of the distribution will be determined.

Figure 10:
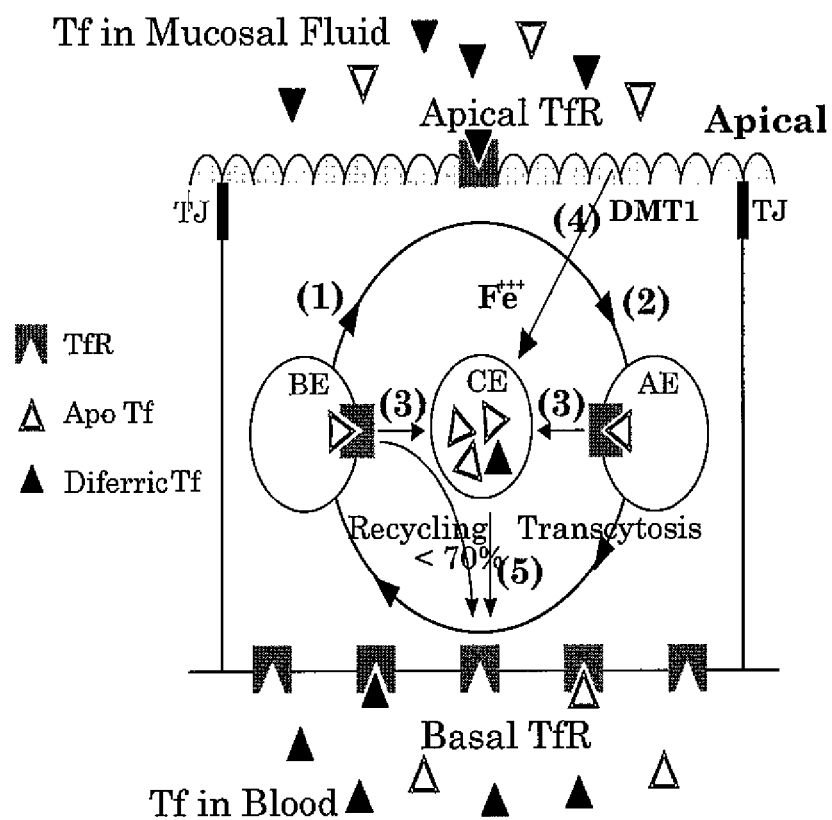
FIG. 10. A hypothetical scheme of the regulatory mechanism for the transport of Tf from the mucosal side of the intestinal epithelial cells to the blood. 1. Miss-sorting of basolateral membrane in basolateral endosomes (BE) would allow a small number of TfR to appear on the apical surface. 2. Orally administered Tf would bind to apical TfR and internalized to apical endosomes (AE), where diferric Tf would be converted to apo-Tf due to the acidification. 3. Apo-Tf in AE would be transported to a common endosome (CE) by a similar process that has been described for apo-Tf in BE [66]. Apo-Tf would be accumulated in CE for a prolonged time. 4. Iron uptake from the mucosal surface via divalent metal transporter 1 (DMT1) could reach CE due to the endocytosis of DMT1 [67]. 5. The conversion of Apo-Tf to diferric Tf in CE would accelerate the transport of diferric Tf from CE to the basolateral membrane via exocytosis, and eventually to be released to the blood [67].

Elucidation of the transport, deposition, and bioavailability of G-CSF-Tf. From the studies described above, the site of retention of the fusion protein in the GI tract should be able to be identified. A retention in the epithelial cells will be consistent with others' findings that apo-Tf can be stored in intestinal epithelial cells as a regulatory pathway for the GI absorption of iron [18]. If this is true, a regulation of Tf-fusion protein absorption should be observed (FIG. 10). In this case, oral administration of fusion protein together with iron, either simultaneously or subsequently, should alter the pharmacodynamic properties and the bioavailability of G-CSF-Tf. Therefore, the study will be modified by including carbonyl iron or ferrous gluconateas an iron supplement. It is expected to see a significantly increased myelopoietic activity at short time, with a decreased sustained effect in long term as dietary iron will increase the release of intracellularly stored apo-Tf to the blood. In addition, the myelopoietic effect of G-CSF-Tf may be able to be boosted by giving the mice a high dose of iron at a defined time point post oral administration of the fusion protein. This finding will provide information for the design of a controlled release system for the oral delivery of protein drugs in the future.

Vetebrate Animals

1. BDF1 mice will be used as an animal model to investigate (a) the transferrin receptor-mediated absorption in intestines and (c) the oral absorption of G-CSF-transferrin fusion proteins conjugates for myelopoietic activity.

(a) For the investigation of transferrin receptor-mediated absorption in intestines, BDF1 mice will be fasted for 12 h, fed biotin-transferrin conjugate or biotin-serum albumin conjugate (control) (1 mg/mouse) with a gavage needle, and subsequently sacrificed in a carbon dioxide chamber. The intestines and livers will be removed and further processed. 4 mice will be used in each group, and the experiment repeated 3 times. Therefore, a total of 24 mice will be used for this study.

(b) For the investigation of G-CSF-Tf fusion proteins, BDF1 mice will be used for the assay of neutrophilic effect. Male BDF1 mice (Charles River Laboratories, Wilmington, Mass.), 6-8 weeks of age, will be used in all animal experiments. The mice will be allowed to acclimate for 5 days. Animal experiments will be compliant with the 'Principles of Laboratory Animal Care' (NIH Publication #85-23) and has been approved by the Institutional Animal Care and Utilization Committee at the University of Southern California. Prior to the dosing, the mice will be fasted for 12 h. The treatment groups will receive a single dose on day 0. Due to the difference in molecular weight, i.e., 20 kD for G-CSF and 100 kD for the fusion protein, animals will receive the dose based on equivalent μmoles. For subcutaneous administration, 5 mg/kg (0.05 μmol/kg) of the fusion protein or 1 mg/kg (0.05 μmol/kg) of G-CSF was injected. For oral administration, 50 mg/kg (0.5 μmol/kg) fusion protein or 10 mg/kg (0.5 μmol/kg) G-CSF will be given via a gavage needle.

Blood samples will be collected daily from the tail vein, diluted 20-fold and lysed in an acidic crystal-violet solution (0.1% crystal violet, 1% acetic acid, in water). The total white blood cell (WBC) count will be determined manually with a hemacytometer. The percentage of polymorphonuclear neutrophils (PMN) among the leukocytes will be determined manually by using Wright-stained blood smear glass slides that will be examined under an Olympus BH-2 microscope. The absolute neutrophil count (ANC) will be determined by multiplying the total WBC count by the PMN percentage.

(c) For pharmacokinetic and biodistribution studies, male BDF-1 mice, 6-8 weeks of age, weighing 22-25 g, will be administered orally with the fusion proteins at doses of 50 mg/kg (10 mg/kg of G-CSF equivalent). The high dose of the fusion protein will be chosen in the pharmacokinetic studies to ensure that a significant and reliable measurement will be obtained. Five mice from each treatment group will be sacrificed at 4 h, 8 h, 12 h, 24 h and 48 h post-administration by the exposure to compressed $CO_2$. The blood samples by cardiac puncture, as well as the liver and intestines of each mouse, will be collected. The liver and intestinal samples will be saved for the further study of tissue localization. Plasma will be isolated from each blood sample and subjected to ELISA analysis of either the intact fusion protein or free G-CSF. Since the myelopoiesis of G-CSF has been shown to have a ceiling effect [53], the dose should be within the linear response range. The simple, non-cleavable fusion protein, G-CSF-Tf, will be used first. Depending on the initial results, the dose of the protein and the time points can be adjusted if necessary. Controls will be done in mice that are injected intravenously with G-CSF-Tf at 1/10 of the oral dose and blood will be collected according to a similar sampling schedule. The plasma half-life of G-CSF-Tf from po and iv treatment will be compared, and a prolonged plasma half-life for the po administration will indicate that a sustained release occurs with the oral absorption route of the fusion protein.

2. Cultured intestinal epithelial cells have been used for the in vitro study of GI drug absorption. However, cell culture systems can only provide information regarding the transport in the epithelial cells. No in vitro system has been established for the investigation of oral peptide absorption which involves not only the permeability of the peptide, but also the GI degradation, mucus interaction, various pH values in different intestinal segments, and the GI transient time. Therefore, measuring the pharmacological activity of the orally administered drug in animal models is still the only conclusive evidence to demonstrate the GI absorption.

240 male, BDF1 mice will be used per year for testing oral myelopoietic effect of G-CSF-Tf fusion proteins. This number is based on the estimation that 24 mice will be needed per each experiment (8 mice in each group of control, G-CSF-treatment, and fusion protein-treatment). Because the background neutrophil number may be different from experiment to experiment, and the myelopoietic response may vary slightly from mouse to mouse, 8 mice/group will be treated in order to obtain statistically significant values. 10 experiments will be done per year, including experiments using dietary iron supplement to control the sustained release of orally absorbed G-CSF-Tf. Therefore, a total of 240 mice will be needed per year for the myelopoiesis assay. 150 BDF-1 mice will be used per year for the pharmacokinetic study of the fusion protein. This number is based on 5 mice per each group, 2 groups per each experiments (iv and po), and 5 time points. Pharmacokinetic studies will be performed in an average of 3 per year. The number of 5 mice per each group is chosen to obtain a minimum number of samples that can provide a statistically significant data.

BDF1 mice is one of very few mouse models that can be used to measure the myelopoietic response to human G-CSF, because most strains of mouse are insensitive to human G-CSF. It should be emphasized that, the age of BDF1 mice is also very important for observing myelopoietic activity, because older mice will not only increase the background ANC, but also decrease the responsiveness to human G-CSF. Therefore, even though non-invasive route is used to treat the mice, i.e., oral administration, the experiment cannot be repeated with the same group of mice for similar study. Therefore, to replace new mice for every experiment is essential to maintain consistent results.

3. An Institutional Animal Care and Use Committee reviews all applications to ensure ethical and humane treatment of animals. All animals will be housed in facilities maintained by the USC Vivaria under the supervision of the Director of the Vivaria, a Veterinarian and his staff of trained support personnel.

4. For myelopoietic assay, approximately 20 μl of blood samples will be collected from the tip of the tail daily up to 3 to 6 days, depending on the specific experiment. This procedure will only cause a minor discomfort when a small amount of blood will be collected from the tip of the tail. The administration of G-CSF or G-CSF-Tf will only increase the immunity of the mice and not cause any pain or adverse effect.

5. Mice will be sacrificed after each experiment. Mice will be sacrificed by the exposure to compressed $CO_2$. This method is recommended by the Panel on Euthanasia of the American Veterinary Medical Association (J. Amer. Vet. Med. Assoc., 202:229-249, 1993).

Example II

In Vitro Characterization of Fusion Protein with a Cyclodisulfide Peptide Linker The fusion protein was produced by transiently transfecting HEK293 cells with plasmids encoding G-CSF-cyclodisuldiepeptide-transferrin (G-C-T). The dithiocyclopeptide linker in the fusion protein contained a thrombin-cutting sequence, PRS, and was characterized by the treatment with or without thrombin and/or dithiothreitol (DTT) followed by anti-G-CSF Western blotting analysis. For the thrombin treatment, 1 μg fusion protein was cleaved by 0.25 NIH unit thrombin when incubated at 20° C. for 16 h. For the DTT treatment, the thrombin-treated or intact fusion protein was added into the reducing loading buffer and boiled for 10 min to reduce the disulfide bond. Protein samples with or without thrombin and/or DTT treatment were then loaded into non-reducing SDS-PAGE and analyzed by anti-G-CSF Western blotting.

The Western blotting result showed that the disulfide bond formed between the two cysteine residues on the linker, and the PRS sequence on the linker can be recognized and cleaved by thrombin.

Figure 11:
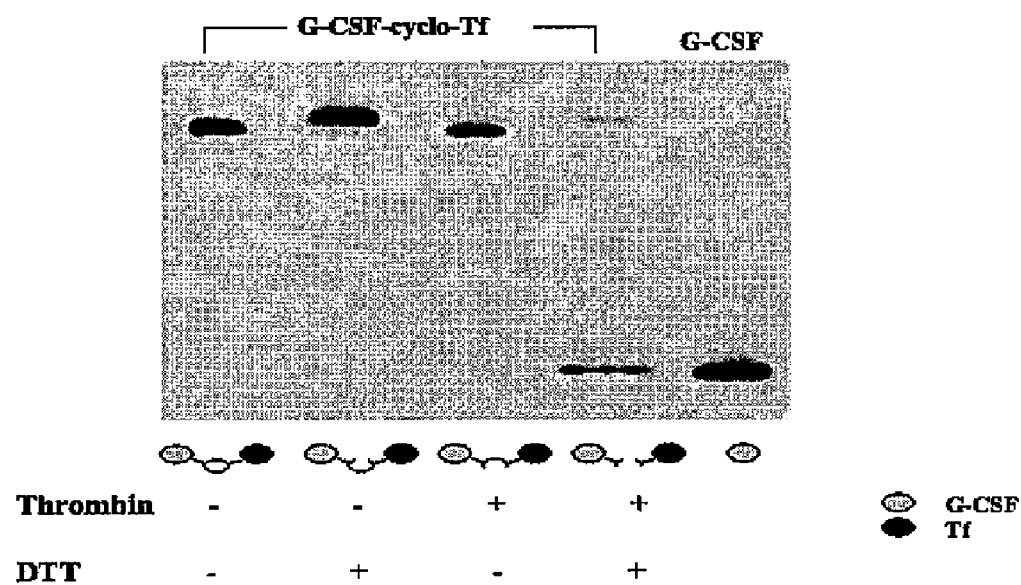
FIG. 11. Anti-G-CSF Western Blotting result for the G-C-T fusion protein with or without thrombin and/or DTT treatment. Lane 1, 2, G-C-T with or without DTT treatment; lane 3, 4, G-C-T with or without DTT treatment after thrombin processing; Lane 5, G-CSF control.
Figure 12:
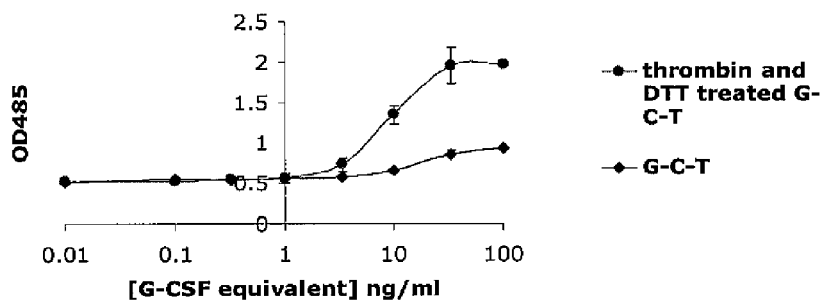
FIG. 12. Evaluation of G-CSF activity of the G-C-T fusion proteins by cell proliferation assay in NFS-60 cells. Cell viability was determined by MTT assay. Samples represent average absorbance ± stdev of the formazan crystals produced in this assay (n=3).

As shown in FIG. 11, G-CSF was released from G-C-T fusion protein by thrombin and DTT treatment to mimic the in vivo reduction. In order to measure the proliferative activity, thrombin and DTT treated G-C-T or intact G-C-T was serially diluted and added to the murine myeloblastic cell line NFS-60. The cells were then incubated at 37° C. in a 5% $CO_2$ incubator for 48 h. A 3-(4,5-dimethylthiazol-2-yl)-2,5-diphenyltetrazolium bromide (MTT) assay was subsequently performed to measure the cell proliferation. FIG. 12 showed that once free G-CSF was released after thrombin and DTT treatment, the fusion protein has an improved biological activity compared to the intact G-C-T.

In Vivo Reduction of Thrombin-Treated G-C-T Fusion Protein

Figure 13:
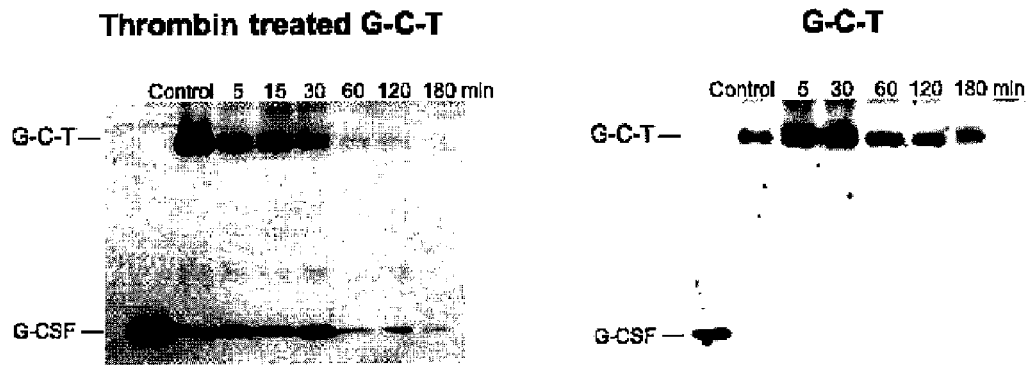
FIG. 13. Upper panel: Anti-G-CSF Western blotting analysis of the blood plasma taken from CF1 mice injected with [left] thrombin treated G-C-T or [right] G-C-T. Plasma samples were taken at different time points after injection. Lower panel: The relative amount of the proteins was quantified using Quality One software (BioRad).
Figure 13:
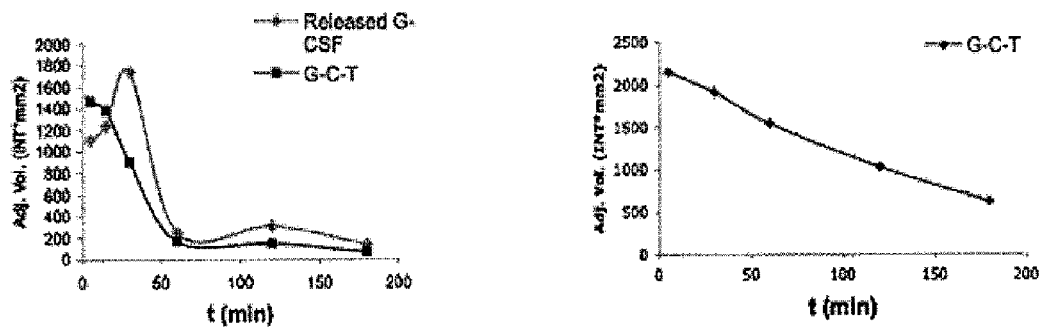

G-C-T fusion protein was treated by thrombin (4 μg protein per NIH unit thrombin) at 20° C. for 16 h to cleave the PRS sequence in the linker cyclopeptide. The thrombin-treated or intact G-C-T fusion protein was injected into CF1 mice via tail vein at the dosage of 1 mg/kg. After injection, blood plasma was taken at different time points and subjected to non-reducing SDS-PAGE followed by anti-G-CSF Western blotting analysis. As shown in FIG. 13, the thrombin-treated G-C-T released free G-CSF in vivo. In contrast, the intact G-C-T didn't release any detectable amount of G-CSF.

Example III

Release of Free G-CSF from G-CSF-Cyclo-Tf Fusion Protein Upon Treatment with Trypsin and Dithiothreitol Method: 0.3 μg G-CSF-cyclo-Tf fusion protein was incubated with different amount of trypsin at 37° C. for 5 min. The fusion protein was then treated with DTT, loaded to reducing SDS-PAGE, and analyzed by anti-G-CSF Western blot.

Figure 14:
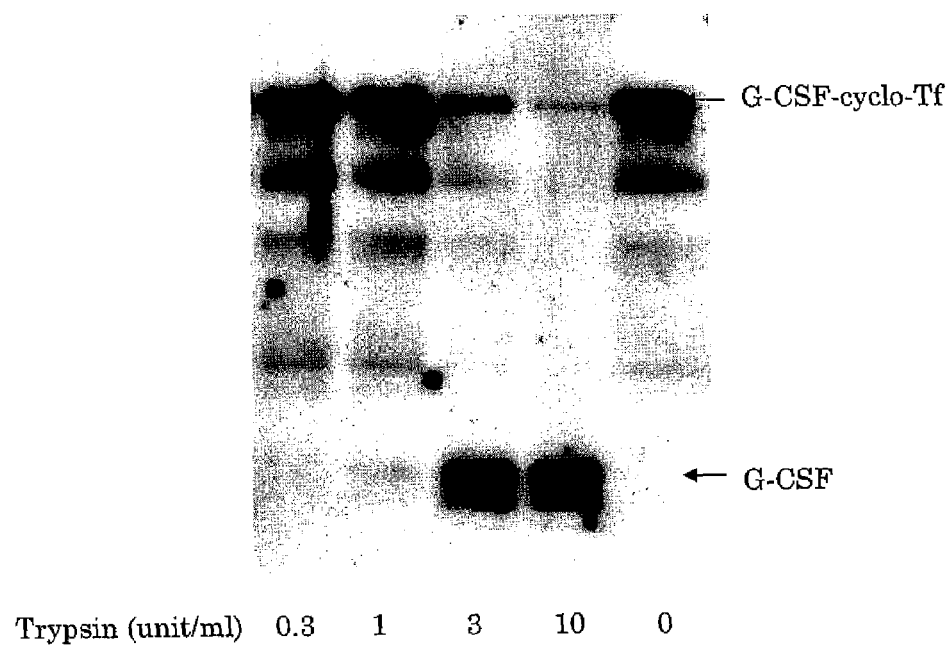
FIG. 14. Release of free G-CSF from G-CSF-cyclo-Tf fusion protein upon treatment with trypsin and dithiothreitol.

Result: Under the suitable trypsin concentration (3 unit/ml, or 10 unit/ml), the cyclic linker was cleaved by trypsin as demonstrated by the appearance of the free G-CSF after DTT reduction (FIG. 14).

LITERATURE CITED

[1] Y. Bai, D. K. Ann and W. C. Shen. Recombinant granulocyte colony-stimulating factor-transferrin fusion protein as an oral myelopoietic agent. Proc Natl Acad Sci USA. 102 (2005) 7292-7296.

[2] M. E. Gosse, J. A. DiMasi and T. Nelson, F R. Recombinant protein and therapeutic monoclonal antibody drug development in the United States from 1980 to 1994. Clin Pharmacol Ther. 60 (1996) 608-618.

[3] Datamonitor. Protein Drug Delivery—Penetrating a growth market. Mar. 7, 2005.

[4] M. Goldberg and I. Gomez-Orellana. Challenges for the oral delivery of macromolecules. Nat Rev Drug Discov. 2 (2003) 289-295.

[5] C. Q. Xia and W. C. Shen. Tyrphostin-8 enhances transferrin receptor-mediated transcytosis in Caco-2-cells and increases hypoglycemic effect of orally administered insulin-transferrin conjugate in diabetic rats. Pharm Res. 18 (2001) 191-5.

[6] A. Widera, Y. Bai and W. C. Shen. The transepithelial transport of a G-CSF-transferrin conjugate in Caco-2 cells and its myelopoietic effect in BDF1 mice. Pharm Res. 21 (2004) 278-284.

[7] P. W. Swaan. Recent advances in intestinal macromolecular drug delivery via receptor-mediated transport pathways. Pharm Res. 15 (1998) 826-834.

[8] W. Shen, Wan J, Ekrami H. Enhancement of polypeptide and protein absorption by macromolecular carriers via endocytosis and transcytosis. Adv Drug Deliv Rev. 8 (1992) 93-113.

[9] K. E. Mostov. Regulation of protein traffic in polarized epithelial cells. Histol Histopathol. 10 (1995) 423-431.

[10] V. H. Lee, A. Yamamoto and U. B. Kompella. Mucosal penetration enhancers for facilitation of peptide and protein drug absorption. Crit. Rev Ther Drug Carrier Syst. 8 (1991) 91-192.

[11] D. Banerjee, P. R. Flanagan, J. Cluett and L. S. Valberg. Transferrin receptors in the human gastrointestinal tract. Relationship to body iron stores. Gastroenterol. 91 (1986) 861-869.

[12] G. J. Anderson, L. W. Powell and J. W. Halliday. Transferrin receptor distribution and regulation in the rat small intestine. Effect of iron stores and erythropoiesis. Gastroenterol. 98 (1990) 576-585.

[13] G. J. Russell-Jones. Use of vitamin B12 conjugates to deliver protein drugs by the oral route. Crit Rev Ther Drug Carrier Syst. 15 (1998) 557-586.

[14] R. R. Crichton. Proteins of iron storage and transport. Adv Protein Chem. 40 (1990) 281-363.

[15] P. R. Azari and R. E. Feeney. Resistance of metal complexes of conalbumin and transferrin to proteolysis and to thermal denaturation. J Biol. Chem. 232 (1958) 293-302.

[16] E. H. Morgan and P. S. Oates. Mechanisms and regulation of intestinal iron absorption. Blood Cells Mol Dis. 29 (2002) 384-399.

[17] W. J. Griffiths and T. M. Cox. Co-localization of the mammalian hemochromatosis gene product (HFE) and a newly identified transferrin receptor (TfR2) in intestinal tissue and cells. J Histochem Cytochem. 51 (2003) 613-624.

[18] R. Flemming. Advances in understanding the molecular basis for the regulation of dietary iron absorption. Curr Opin Gastroenterol. 21 (2005) 201-206.

[19] S. Parkkila, O, Niemela, R. S. Britton, R. E. Fleming, A. Waheed, B. R. Bacon and W. S. Sly. Molecular aspects of iron absorption and HFE expression. Gastroenterol. 121 (2001) 1489-1496.

[20] E. Rodgiguez-Boulan and W. Nelson. Morphogenesis of the polarized epithelial cell phenotype. Science. 245 (1989) 718-725.

[21] A. Widera, F. Norouziyan and W. C. Shen. Mechanisms of TfR-mediated transcytosis and sorting in epithelial cells and applications toward drug delivery. Adv Drug Deliv Rev. 55 (2003) 1439-1466.

[22] P. Friden. Receptor-mediated transport of therapeutics across the blood-brain barrier. Neurosurgery. 35 (1994) 294-298.

[23] M. Weaver and D. W. Laske. Transferrin Receptor Ligand-Targeted Toxin Conjugate (Tf-CRM107) for Therapy of Malignant Gliomas. J Neuro-Oncol. 65 (2003) 3-14.

[24] M. Singh. Transferrin as a targeting ligand for liposomes and anticancer drugs. Curr Pharm Des. 5 (1999) 443-451.

[25] B. Sonnichsen, S. De Renzis, E. Nielsen, J. Rietdorf and M. Zerial. Distinct membrane domains on endosomes in the recycling pathway visualized by multicolor imaging of Rab4, Rab5, and Rab11. J Cell Biol. 149 (2000) 901-914.

[26] E. M. van Dam, T. ten Broeke, K. Jansen, P. Spijkers and W. Stoorvogel. Endocytosed Transferrin Receptors Recycle via Distinct Dynamin and Phosphatidylinositol 3-Kinase-dependent Pathways. J Biol Chem. 277 (2002) 48876-48883.

[27] D. Shah and W. C. Shen. The paradox of transferrin receptor-mediated drug delivery—intracellular targeting or transcellular transport? J Drug Target. 3 (1995) 243-245.

[28] D. Shah and W. C. Shen. The establishment of polarity and enhanced transcytosis of transferrin receptors in enterocyte-like Caco-2 cells. J Drug Target. 2 (1994) 93-99.

[29] A. Widera, K. J. Kim, E. D. Crandall and W. C. Shen. Transcytosis of GCSF-transferrin across rat alveolar epithelial cell monolayers. Pharm Res. 20 (2003) 1231-1238.

[30] C. Q. Xia, J. Wang and W. C. Shen. Hypoglycemic effect of insulin-transferrin conjugate in streptozotocin-induced diabetic rats. J Pharmacol Exp Ther. 295 (2000) 594-600.

[31] E. Park, R. M. Starzyk, J. P. McGrath, T. Lee, J. George, A. J. Schutz, P. Lynch and S. D. Putney. Production and characterization of fusion proteins containing transferrin and nerve growth factor. J Drug Target. 6 (1998) 53-64.

[32] M. Brazil. Research Highlights: Transferrin' the load. Nature Rev. Drug Disc. 4 (2005) 537.

[33] D. L. Newton, Y. Xue, K. A. Olson, J. W. Fett and S. M. Rybak. Angiogenin Single-Chain Immunofusions: Influence of Peptide Linkers and Spacers between Fusion Protein Domains. Biochemistry. 35 (1996) 545-553.

[34] R. J. Jenny, K. G. Mann and R. L. Lundblad. A critical review of the methods for cleavage of fusion proteins with thrombin and factor Xa. Protein Expression and Purification. 31 (2003) 1-11.

[35] Y. Bai and W. C. Shen. Improving the oral efficacy of recombinant granulocyte colony-stimulating factor and transferrin fusion protein by spacer optimization. Pharm Res (2006) in press.

[36] G. Saito, J. A. Swanson and K. D. Lee. Drug delivery strategy utilizing conjugation via reversible disulfide linkages: role and site of cellular reducing activities. Adv Drug Del Rev 55 (2003) 199-215.

[37] V. H. L. Lee. Enzymatic barriers in peptide and protein absorption. Crit Rev Ther Drug Carrier Sys 7 (1988) 69-97.

[38] S. Kaminogawa. Food allergy, oral tolerance and immunomodulation—their molecular and cellular mechanisms. Biosci Biotechnol Biochem. 60 (1996) 1749-1756.

[39] A. Widera, K. Beloussow, K. J. Kim, E. D. Crandall and W. C. Shen. Phenotype-dependent synthesis of transferrin receptor in rat alveolar epithelial cell monolayers. Cell Tissue Res. 312 (2003) 313-318.

[40] C. J. Lim and W. C. Shen. Transferrin-oligomers as potential carriers in anticancer drug delivery. Pharm Res. 21 (2004) 1985-1992.

[41] C. J. Lim and W. C. Shen. Comparison of monomeric and oligomeric transferrin as potential carrier in oral delivery of protein drugs. J Control Release. 106 (2005) 273-286.

[42] H. A. Huebers and C. A. Finch. The physiology of transferrin and transferrin receptors. Physiol Rev 67 (1987) 520-582.

[43] L. M. Hollingshead and K. L. Goa. Recombinant granulocyte colony-stimulating factor (rG-CSF): A review of its pharmacological properties and prospective role in neutropenic conditions. Drugs 42 (1991) 300-330.

[44] P. S. Oates, C. Thomas and E. H. Morgan. Transferrin receptor activity and localisation in the rat duodenum. Pflugers Arch. 440 (2000) 116-124.

[45] B. F. LeBonniec, T. Myles, T. Johnson, C. G. Knight, C. Tapparelli and S. R. Stone. Characterization of the $P_2'$ and $P_3'$ specificities of thrombin using fluorescene-quenched substrates and mapping of the subsites by mutagenesis. Biochemistry 35 (1996) 7114-7122.

[46] R. Arai, H. Ueda, A. Kitayama, N. Kamiya and T. Nagamune. Design of the linkers which effectively separate domains of a bifunctional fusion protein. Protein Eng. 14 (2001) 529-532.

[47] S. Marqusee and R. L. Baldwin. *Helix* Stabilization by Glu-Lys+ Salt Bridges in Short Peptides of De novo Design. Proc Natl Acad Sci USA. 84 (1987) 8898-8902.

[48] L. Guo, J. Wang, S. Qian, X. Yan, R. Chen and G. Meng. Construction and Structural Modeling of a Single-Chain Fv-Asparaginase Fusion Protein to Proteolysis. Biotechnol Bioeng. 70 (2000) 456-463.

[49] Zhang Y. Y. and H. M. M. Expression and Functional Characterization of *Escherichia coli* NusA and Lambda Q as Glutathione S-Transferase Fusion Proteins. Protein Expression and Purification. 6 (1995) 625-631.

[50] C. H. Fynbo, R. H. Lorentsen, M. Etzerodt, H. C. Thogersen and T. L. Holtet. Characterization of a recombinant granzyme B derivative as a "restriction" protease. Protein Expression and Purification. 39 (2005) 209-218.

[51] E. D. B. Clark, D. Hevehan, S. Szela and J. Maachupalli-Reddy. Oxidative renaturation of hen egg-white lysozyme. Folding vs aggregation. Biotechnol Prog 14 (1998) 47-54.

[52] L. R. Denizot F. Rapid calorimetric assay for cell growth and survival. Modifications to the tetrazolium dye procedure giving improved sensitivity and reliability. J Immun Meth. 89 (1986) 271-277.

[53] M. Winkler, J. Price, P. Foglesong and W. West. Biodistribution and plasma survival in mice of anti-melanoma monoclonal antibody cross-linked to OKT3. Cancer Immunol Immunother. 31 (1990) 278-284.

[54] G. Wu, R. F. Barth, W. Yang, M. Chatterjee, W. Tjarks, M. J. Ciesielski and R. A. Fenstermaker. Site-Specific Conjugation of Boron-Containing Dendrimers to Anti-EGF Receptor Monoclonal Antibody Cetuximab (IMC-C225) and Its Evaluation as a Potential Delivery Agent for Neutron Capture Therapy. Bioconjugate Chem. 15 (2004) 185-194.

[55] P. Sacks and D. Honchin. Comparative bioavailability of element iron powders for repair of iron deficiency anemia in rats. Studies of efficiency and toxicity of carbonyl iron. Amer. J. Clin. Natr. 31 (1978) 566-573.

[56] J. Macri and K. Adeli. Development of an amplified enzyme-linked immunosorbent assay for sensitive measurement of apolipoprotein B in plasma and tissue culture media. European Journal Of Clinical Chemistry And Clinical Biochemistry: Journal Of The Forum Of European Clinical Chemistry Societies. 31 (1993) 441-446.

[57] C.-K. Chang, T. K. Tso, J. T. Snook, W. B. Zipf and R. A. Lozano. Sandwich enzyme-linked immunosorbent assay for plasma cholesteryl ester transfer protein concentration. Clin Biochem. 32 (1999) 257-262.

[58] M. Koenigsmann, K. Jentsch-Ullrich, M. Mohren, E. Becker, M. Heim, and A. Franke. The role of diagnosis in patients failing peripheral blood progenitor cell mobilization. Transfusion 44 (2004) 777-784.

[59] Lansdown A B, Dayan A D. Alterations in crypt cell populations in the small intestine as an early toxic response to sub-acute ethanol administration. Arch Toxicol. 59 (1987) 448-452.

[60] Anthony A, Dhillon A P, Nygard G, Hudson M, Piasecki C, Strong P, Trevethick M A, Clayton N M, Jordan C C, Pounder R E, et al. Early histological features of small intestinal injury induced by indomethacin. Aliment Pharmacol Ther. 7 (1993) 29-39.

[61] Zhao Z, Hyun J S, Satsu H, Kakuta S, Shimizu M. Oral exposure to cadmium chloride triggers an acute inflammatory response in the intestines of mice, initiated by the over-expression of tissue macrophage inflammatory protein-2 mRNA. Toxicol Lett. 164 (2006) 144-154.

[62] H. A. Huebers, E. Huebers, E. Csiba, W. Rummel and C. A. Finch. The significance of transferrin for intestinal iron absorption. Blood. 61 (1983) 283-90.

[63] P. Aisen. Transferrin metabolism and the liver. Semin Liver Dis. 4 (1984) 193-206.

[64] G. Peters, H. Keberle, K. Schmid and H. Brunner. Distribution and renal excretion of desferrioxamine and ferrioxamine in the dog and in the rat. Biochem Pharmacol. 15 (1966) 93-109.

[65] H. Tanaka and T. Kaneko. Pharmacokinetics of recombinant human granulocyte colony-stimulating factor in mice. Blood. 79 (1992) 536-539.

[66] E. J. Hughson and C. R. Hopkins. Endocytic pathways in polarized Caco-2 cells: identification of an endosomal compartment accessible from both apical and basolateral surfaces. J Cell Biol. 110 (1990) 337-348.

[67] Y. Ma, R. D. Specian, K. Y. Yeh, M. Yeh, J. Rodriguez-Paris and J. Glass. The transcytosis of divalent metal transporter 1 and apo-transferrin during iron uptake in intestinal epithelium. Am J Physiol Gastrointest Liver Physiol. 283 (2002) G965-974.

[68] J. A. Posey, et al. A Phase I trial of the single-chain immunotoxin SGN-10 (BR96 sFV-PE-40) in patients with advanced solid tumors. Clin. Cancer Res 8 (2002) 3092-3099.

While the foregoing has been described in considerable detail and in terms of preferred embodiments, these are not to be construed as limitations on the disclosure. Modifications and changes that are within the purview of those skilled in the art are intended to fall within the scope of the invention.

What is claimed is:

1. A polypeptide comprising:
   a first protein domain;
   a second protein domain; and
   a dithiocyclopeptide spacer containing at least one protease cleavage site, wherein the dithiocyclopeptide is exogenous relative to the first or second protein domain, and wherein the first and second protein domains are operably linked by the dithiocyclopeptide, and
   wherein the dithiocyclopeptide contains LEAGCKNFFPRSFTSCGSLE (SEQ ID NO: 1) or LEAGCPRSFWTFPRSCGSLE (SEQ ID NO: 2).

2. The polypeptide of claim 1, wherein the dithiocyclopeptide is cyclized by a disulfide bond.

3. The polypeptide of claim 2, wherein the dithiocyclopeptide is cleaved by a protease at the protease cleavage site.

4. The polypeptide of claim 1, wherein the dithiocyclopeptide is cleaved by a protease at the protease cleavage site.

5. The polypeptide of claim 1, wherein the first protein domain is a granulocyte-colony stimulating factor (G-CSF) domain.

6. The polypeptide of claim 5, wherein the second protein domain is a transferrin (Tf) domain.

7. The polypeptide of claim 1, wherein the second protein domain is a Tf domain.

8. The polypeptide of claim 1, wherein the polypeptide is a recombinant polypeptide.

9. A nucleic acid comprising a DNA sequence encoding the polypeptide of claim 8.

10. A cell comprising the nucleic acid of claim 9.

11. A method of producing a polypeptide, comprising cultivating the cell of claim 10 under conditions that allow expression of the polypeptide.

12. The method of claim 11, further comprising collecting the polynucleotide.

13. The method of claim 12, further comprising cleaving the polypeptide with the protease.

14. A method of delivering protein domains into a cell, comprising contacting a cell with the polypeptide of claim 1 under conditions that allow transport of the polypeptide into the cell, wherein the disulfide bond in the dithiocyclopeptide is reduced during the transport or within the cell, thereby separating the first protein domain from the second protein domain.

15. The method of claim 14, wherein the first protein domain is a G-CSF domain.

16. The method of claim 15, wherein the second protein domain is a Tf domain.

17. The method of claim 16, wherein the cell expresses transferrin receptor (TfR).

18. The method of claim 14, wherein the second protein domain is a Tf domain.

19. The method of claim 18, wherein the cell expresses TfR.

* * * * *

SEQUENCE LISTING

```
<160> NUMBER OF SEQ ID NOS: 6

<210> SEQ ID NO 1
<211> LENGTH: 20
<212> TYPE: PRT
<213> ORGANISM: Artificial
<220> FEATURE:
<223> OTHER INFORMATION: Contained in dithiocyclopeptide
```

-continued

```
<400> SEQUENCE: 1

Leu Glu Ala Gly Cys Lys Asn Phe Phe Pro Arg Ser Phe Thr Ser Cys
1               5                   10                  15

Gly Ser Leu Glu
            20

<210> SEQ ID NO 2
<211> LENGTH: 20
<212> TYPE: PRT
<213> ORGANISM: Artificial
<220> FEATURE:
<223> OTHER INFORMATION: Contained in dithiocyclopeptide

<400> SEQUENCE: 2

Leu Glu Ala Gly Cys Pro Arg Ser Phe Trp Thr Phe Pro Arg Ser Cys
1               5                   10                  15

Gly Ser Leu Glu
            20

<210> SEQ ID NO 3
<211> LENGTH: 11
<212> TYPE: PRT
<213> ORGANISM: Artificial
<220> FEATURE:
<223> OTHER INFORMATION: Thrombin digested cyclopeptide spacer

<400> SEQUENCE: 3

Leu Glu Ala Gly Cys Lys Asn Phe Phe Pro Arg
1               5                   10

<210> SEQ ID NO 4
<211> LENGTH: 9
<212> TYPE: PRT
<213> ORGANISM: Artificial
<220> FEATURE:
<223> OTHER INFORMATION: Thrombin digested cyclopeptide spacer

<400> SEQUENCE: 4

Ser Phe Thr Ser Cys Gly Ser Leu Glu
1               5

<210> SEQ ID NO 5
<211> LENGTH: 60
<212> TYPE: DNA
<213> ORGANISM: Artificial
<220> FEATURE:
<223> OTHER INFORMATION: Insert of the disulfide cyclopeptide linker

<400> SEQUENCE: 5
ctcgaggctg gttgtaaaaa ttttttccct cgttcttttα ctagttgtgg ttctctcgag      60

<210> SEQ ID NO 6
<211> LENGTH: 14
<212> TYPE: PRT
<213> ORGANISM: Artificial
<220> FEATURE:
<223> OTHER INFORMATION: Somatostatin

<400> SEQUENCE: 6

Ala Gly Cys Lys Asn Phe Phe Trp Lys Thr Phe Thr Ser Cys
1               5                   10
```